(12) United States Patent
Branch, Jr. et al.

(10) Patent No.: US 9,993,630 B2
(45) Date of Patent: Jun. 12, 2018

(54) SUBDURAL DRAINAGE CATHETERS WITH SELF CONTAINED MECHANISM FOR RESTORATION OF FLOW FOLLOWING CATHETER OBSTRUCTION

(71) Applicant: Wake Forest University Health Sciences, Winston-Salem, NC (US)

(72) Inventors: Charles L. Branch, Jr., Advance, NC (US); John P. Eikman, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 451 days.

(21) Appl. No.: 14/778,340

(22) PCT Filed: Mar. 21, 2014

(86) PCT No.: PCT/US2014/031441
§ 371 (c)(1),
(2) Date: Sep. 18, 2015

(87) PCT Pub. No.: WO2014/153508
PCT Pub. Date: Sep. 25, 2014

(65) Prior Publication Data
US 2016/0166812 A1 Jun. 16, 2016

Related U.S. Application Data

(60) Provisional application No. 61/803,952, filed on Mar. 21, 2013.

(51) Int. Cl.
*A61M 27/00* (2006.01)
*A61M 39/02* (2006.01)
(Continued)

(52) U.S. Cl.
CPC ............ *A61M 27/00* (2013.01); *A61M 39/02* (2013.01); *A61M 25/02* (2013.01); *A61M 39/08* (2013.01);
(Continued)

(58) Field of Classification Search
CPC .... A61M 27/006; A61M 25/02; A61M 39/02; A61M 2210/0693; A61M 2025/0019; A61M 2039/0276; A61M 2039/025
See application file for complete search history.

(56) References Cited

U.S. PATENT DOCUMENTS 5,385,541 A  1/1995 Kirsch et al.
5,836,928 A  11/1998 Gerber et al.
(Continued)

*Primary Examiner* — Leslie Deak
(74) *Attorney, Agent, or Firm* — Myers Bigel, P.A.

(57) ABSTRACT

A subdural drainage system includes: (a) a subdural drainage device having an opening formed therethrough, said subdural drainage device having an upper portion, a body portion, and a lower portion; (b) a housing having an upper portion and lower portion, with said housing connected to said subdural drainage device; said housing movable between (i) a first configuration and (ii) a second configuration; and (c) an elongated element positioned inside said housing, said elongated element having an upper portion, a lower portion and a deformable member connected to the lower portion; said elongated element being configured such that said elongated element is moved between (i) a retracted position with said elongated element inside a portion of said subdural drainage device and said deformable member inside said housing, and (ii) an extended position with said elongated element extending through said subdural drainage device such that said deformable member automatically extends to an extended, deformed position in which blockages are disrupted in the subdural drainage device when said housing is moved between said first and second housing (Continued)

configurations; and (d) an external drain opening formed on either said subdural drainage device or said housing.

18 Claims, 20 Drawing Sheets

(51) Int. Cl.
*A61M 39/08* (2006.01)
*A61M 25/02* (2006.01)
*A61M 25/00* (2006.01)

(52) U.S. Cl.
CPC .............. *A61M 2025/0019* (2013.01); *A61M 2025/0233* (2013.01); *A61M 2039/025* (2013.01); *A61M 2039/0276* (2013.01); *A61M 2210/0687* (2013.01)

(56) References Cited

U.S. PATENT DOCUMENTS

| | | |
|---|---|---|
| 6,283,940 B1 | 9/2001 | Mulholland |
| 6,855,126 B2 | 2/2005 | Flinchbaugh |
| 6,923,799 B1 | 8/2005 | Asfora |
| 2011/0282263 A1 | 11/2011 | Branch, Jr. et al. |

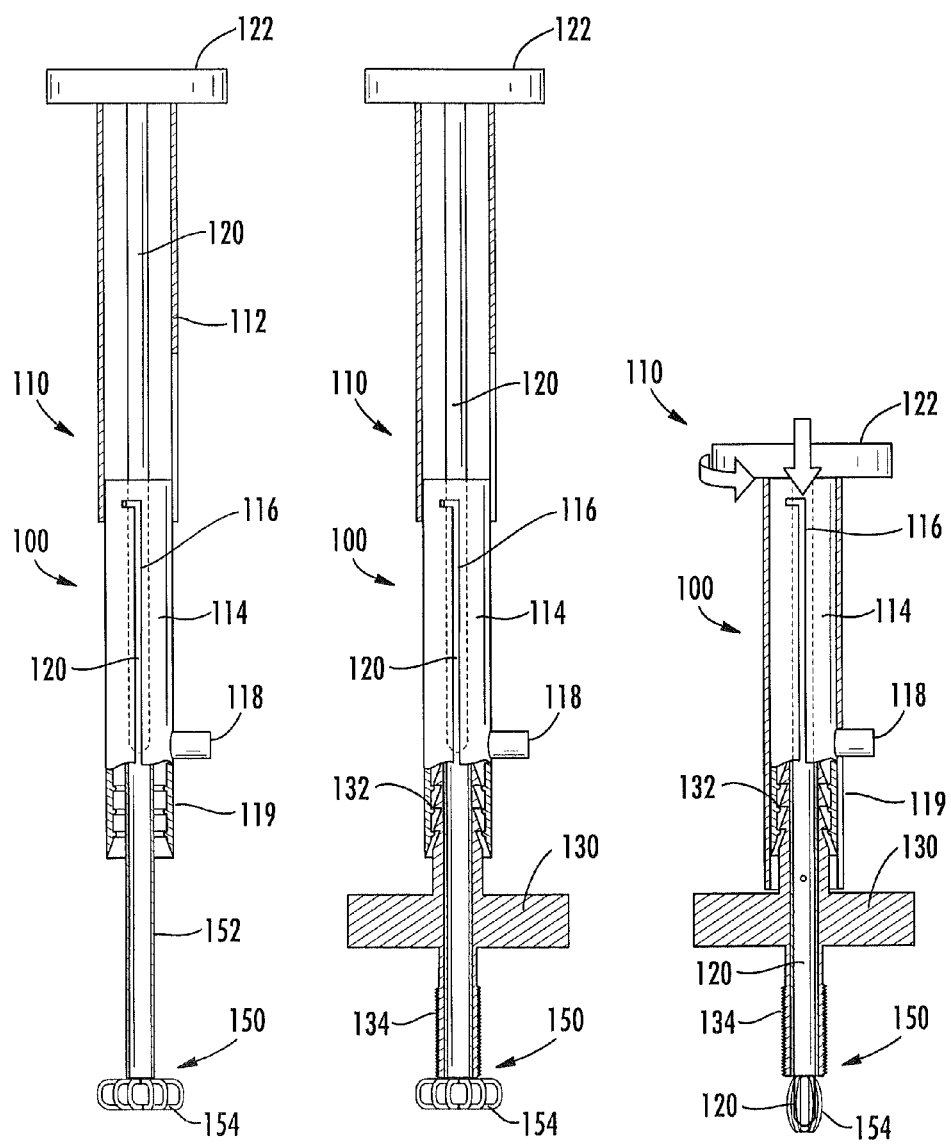

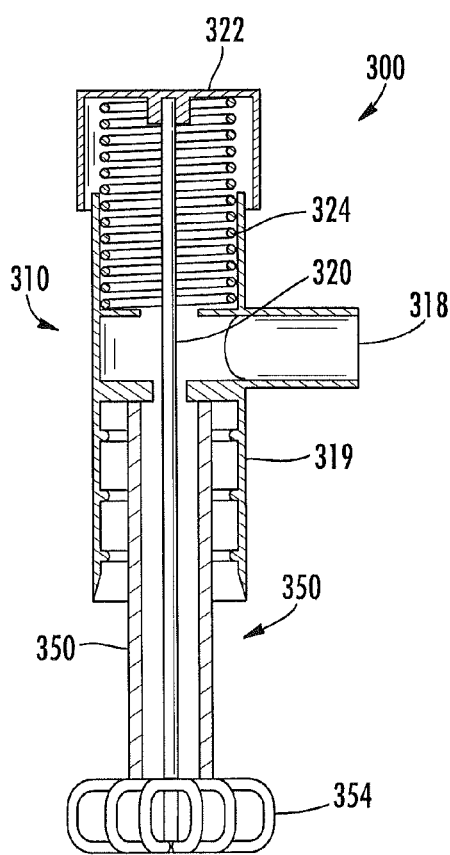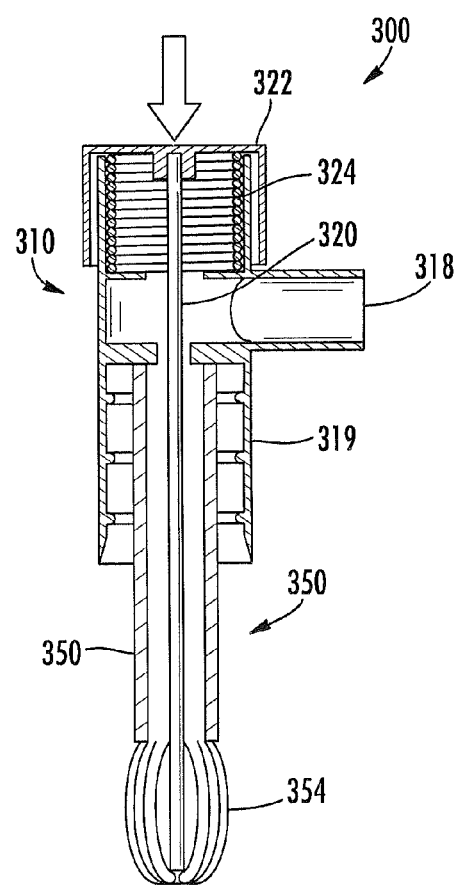
FIG. 8A
FIG. 8B

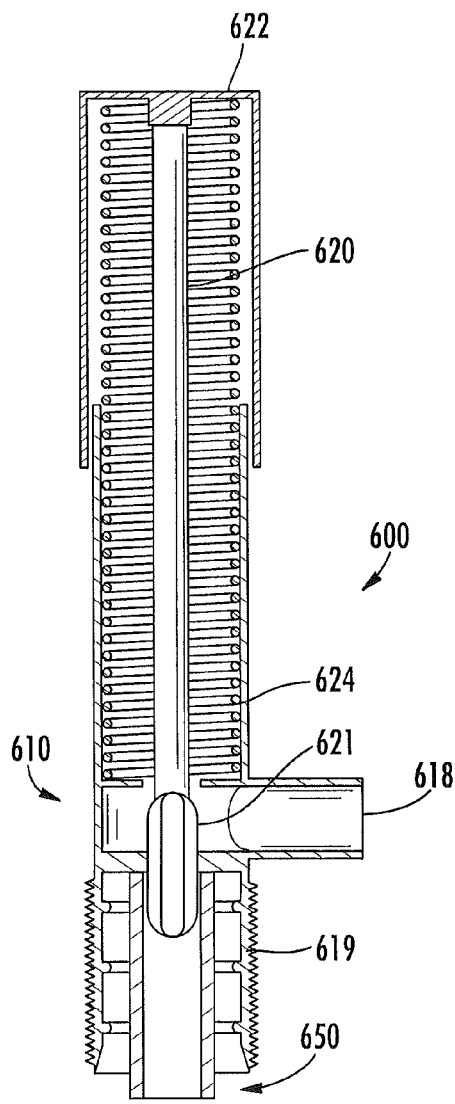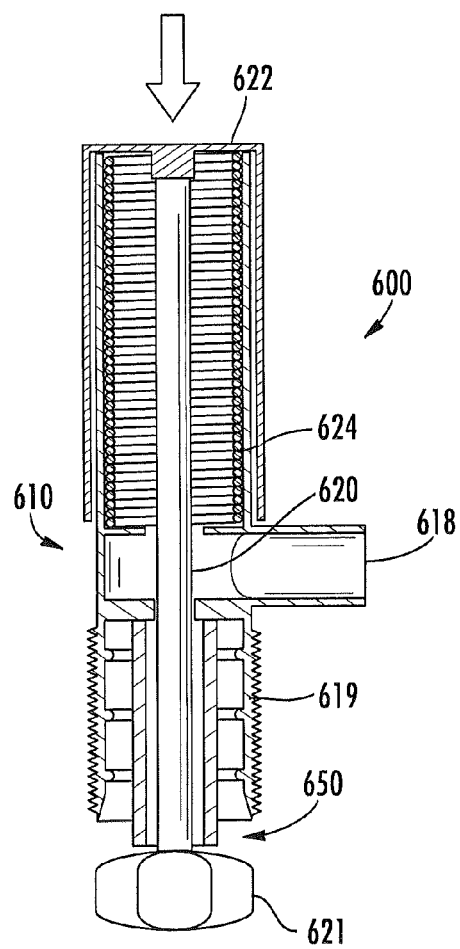
FIG. 11A
FIG. 11B

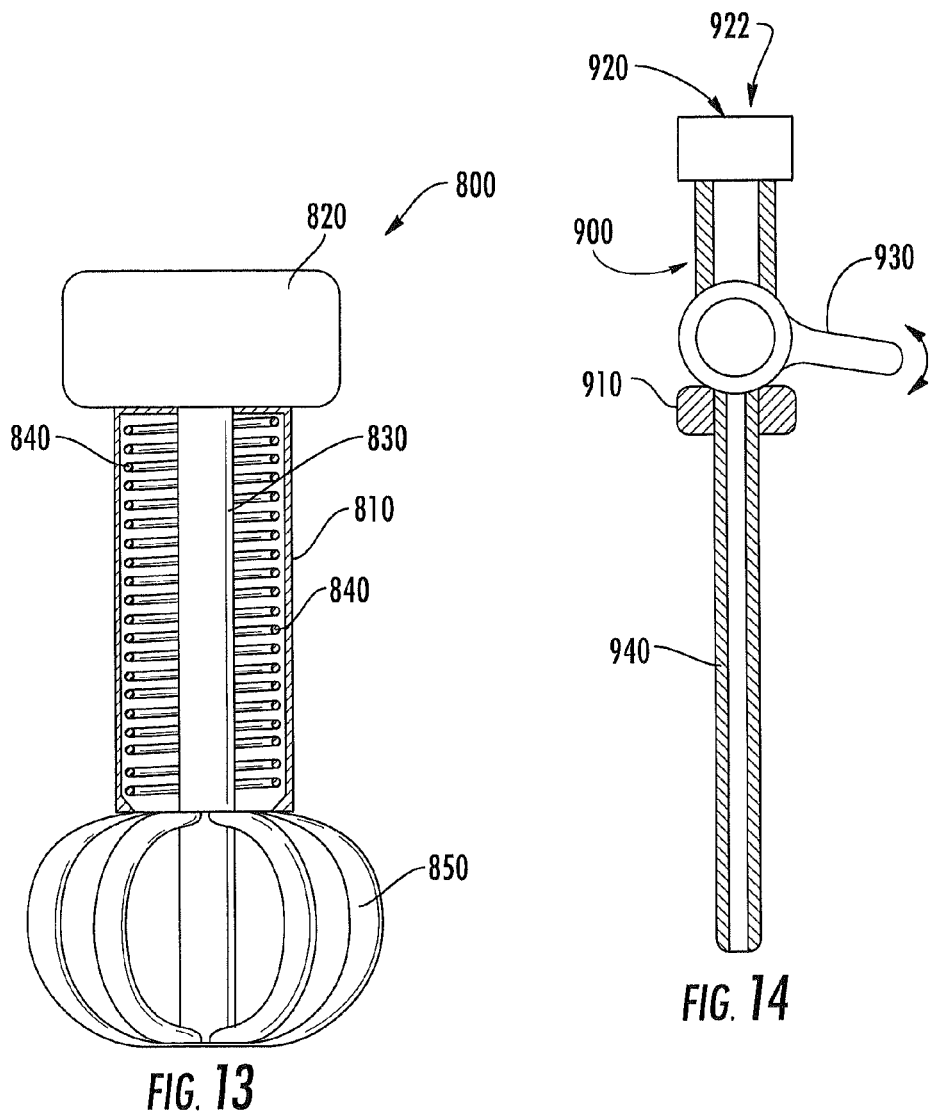

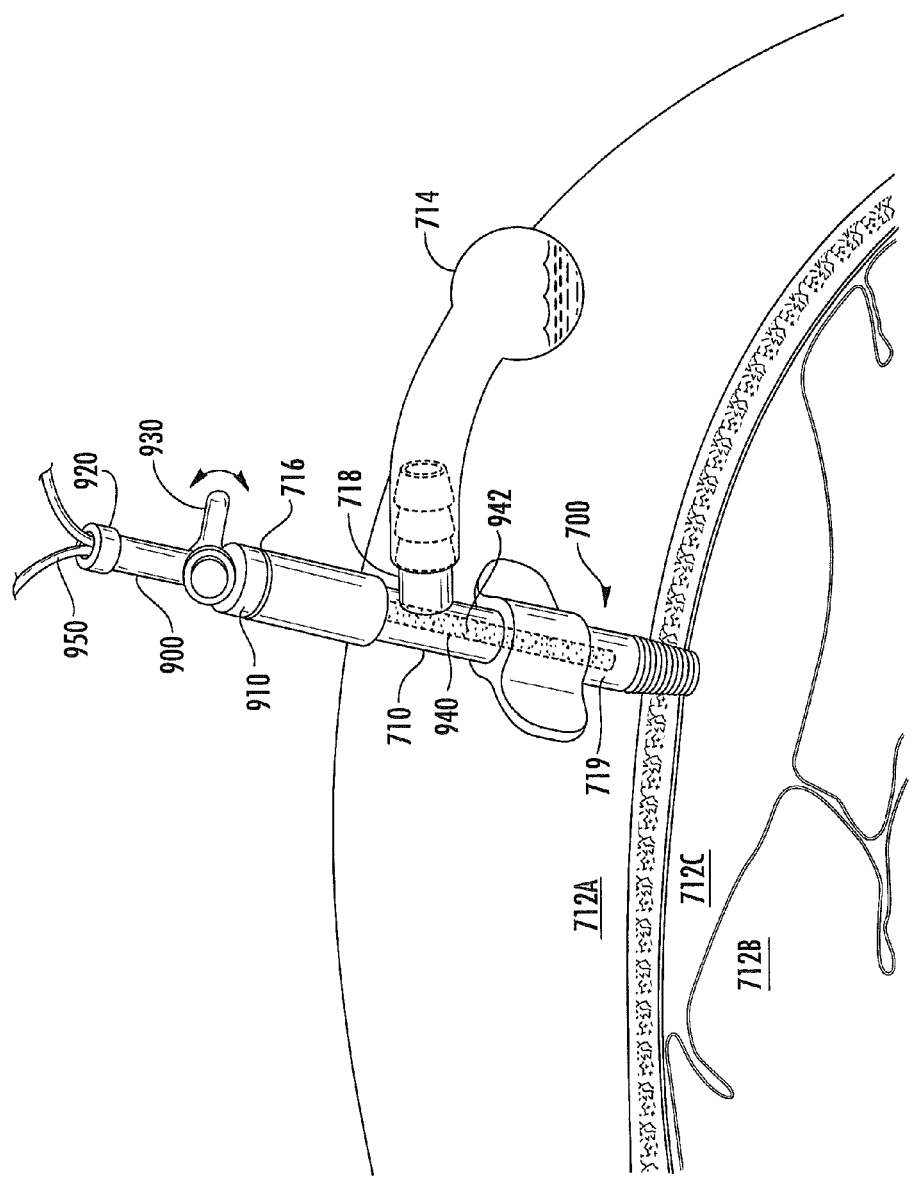

SUBDURAL DRAINAGE CATHETERS WITH SELF CONTAINED MECHANISM FOR RESTORATION OF FLOW FOLLOWING CATHETER OBSTRUCTION

RELATED APPLICATIONS

This application is a 35 U.S.C. § 371 national phase application of PCT International Application No. PCT/US2014/031441, filed Mar. 21, 2014, which claims priority to U.S. Provisional Application Ser. No. 61/803,952, filed Mar. 21, 2013, and is related to U.S. application Ser. No. 13/848,285, filed Mar. 21, 2013, which is a continuation of U.S. application Ser. No. 13/130,238, filed Aug. 2, 2011, which will issue as U.S. Pat. No. 8,403,878 on Mar. 26, 2013, and is a 35 U.S.C. § 371 national phase application of PCT Application PCT/US2009/065282, filed Nov. 20, 2009, and published in English on May 27, 2010, as International Publication No. WO 2010/059915 A1, and which claims the benefit under 35 U.S.C. § 119(e) of U.S. Provisional Patent Application Ser. No. 61/116,525, filed Nov. 20, 2008, the disclosure of each of which is incorporated herein by reference in its entirety. PCT International Application No. PCT/US2014/031441 is published in English as PCT Publication No. WO 2014/153508.

FIELD OF THE INVENTION

The present invention concerns medical devices in general, and particularly concerns devices for the treatment of subdural hematoma.

BACKGROUND OF THE INVENTION

Subdural hematomas continue to be a challenging set of pathology for neurosurgeons given today's aging population. Patients with symptomatic subacute and chronic subdural hematomas are frequently elderly and commonly have multiple coexisting medical conditions. Typically patients present after a remote history of trauma, though often trivial, with progressive neurologic deficits including hemiparesis, gait instability, and cognitive decline to name a few: Ramachandran R, Thimmappa H. "Chronic subdural hematomas—causes of morbidity and mortality." Surg Neurol 2007:67; 367-373. The mortality rate for this pathology even with treatment, often cited at a range of 2-6%, is significant given the frequency of symptomatic presentation. Sucu H K, Gokmen M, Ergin A, Bezircioglu, Gokemn A. "Is there a way to avoid surgical complications of twist drill craniostomy for evacuation of a chronic subdural hematoma." Acta Neurochir (Wien) 2007; 149:597-599; Ernestus R I, Beldzinski P, Lanfermann H, Klug N. "Chronic subdural hematoma: Surgical treatment and outcome in 104 patients." Surg Neurol 1997; 48:220-225; Mellergard P, Wisten O. "Operations and re-operations for chronic subdural haematomas during a 25-year period in a well defined population: Acta Neurochir (Wien) 1996; 138:708-713; and Merlicco G, Pierangeli E, di Padova P L. "Chronic subdural hematomas in adults: prognostic factors." Analysis of 70 cases. Neurosurg Rev 1995; 18:247-251. Multiple treatment modalities have been described and advocated in the literature. The most extreme is a standard craniotomy under general anesthesia for hematoma evacuation and membrane removal, if present. Alternatively, isolated or multiple bur holes may be drilled to permit hematoma irrigation and removal. More recently, placement of a tangential drainage catheter within the subdural space via a twist-drill craniostomy had been practiced typically under monitored sedation, but catheter obstruction and cessation of flow is often encountered.

A subdural evacuation port system (or "SEPS") available from Medtronic, Inc., Minneapolis, Minn., has seen recent use. As illustrated in FIG. 1, a SEPS device 10 is essentially a hollow screw placed in the skull 20 which communicates with the subdural space 22 and is attached to closed system suction device (not shown). Asfora W T, Schwebach L. "A modified technique to treat chronic and subacute subdural hematoma: technical report." Surg Neural 2003; 59:329-332. While the device 10 has appeared more successful that the tangential subdural catheter technique and can be performed without general anesthesia, it is potentially complicated by portal obstruction prior to adequate hematoma evacuation.

Indeed, recent experience of one surgical group with the SEPS device indicates that approximately one third of patients treated had less than half of the hematoma volume evacuated. This subsequently resulted in approximately one quarter of the patients requiring an additional surgical procedure to adequately evacuate the hematoma due to inability to restore drainage of fluid through this system after it became occluded. One could open the system to clear occlusions by insert a trochar, but this potentially breaks sterility, and insertion of a trochar or other tool raises the potential of injuring underlying brain tissue. Hence, there is a need for new devices for the treatment of subdural hematoma.

SUMMARY OF THE INVENTION

According to some embodiments of the present invention, a subdural drainage system includes: (a) a subdural drainage device having an opening formed therethrough, said subdural drainage device having an upper portion, a body portion, and a lower portion; (b) a housing having an upper portion and lower portion, with said housing connected to said subdural drainage device; said housing movable between (i) a first configuration and (ii) a second configuration; and (c) an elongated element positioned inside said housing, said elongated element having an upper portion, a lower portion and a deformable member connected to the lower portion; said elongated element being configured such that said elongated element is moved between (i) a retracted position with said elongated element inside a portion of said subdural drainage device and said deformable member inside said housing, and (ii) an extended position with said elongated element extending through said subdural drainage device such that said deformable member automatically extends to an extended, deformed position in which blockages are disrupted in the subdural drainage device when said housing is moved between said first and second housing configurations; and (d) an external drain opening formed on either said subdural drainage device or said housing.

In some embodiments, the deformable member has a diameter that is greater than a diameter of said housing when said deformable member is in the extended, deformed position.

In some embodiments, the elongated element comprises a stylet. In some embodiments, the elongated element comprises a catheter.

In some embodiments, the elongated element and the housing are connected to one another; and the elongated element is slidably received in said catheter opening. In some embodiments, the elongated element, the deformable member and the housing are removably received in the subdural drainage device.

In some embodiments, a drug delivery device is removably receivable in said subdural drainage device.

In some embodiments, the housing comprises a rigid telescoping housing.

In some embodiments, the housing comprises a biasing member positioned to bias the enclosed housing in one of said first or second configurations.

In some embodiments, the subdural drainage device lower portion has self-tapping threads formed thereon; and the subdural drainage device comprises an enlarged grasping portion for manually threading the lower portion into the skull of a subject.

In some embodiments, a reservoir is connected to the external drain opening.

In some embodiments, the housing provides a sealed enclosure when the system is connected to a skull of a subject.

In some embodiments, an occlusion-removal apparatus for use with a subdural drainage device includes (a) an elongated element configured to be inserted in said subdural drainage device; said elongated element having a proximal end and a distal end, with said elongated element having a drain lumen formed therein; and with said distal end having a deformable member having subdural drain openings formed therein, said drain openings in fluid communication with said drain lumen; (b) a housing connected to said elongated element and having an upper portion and lower portion; and wherein said elongated element is movable between (i) a retracted position with said elongated element inside a portion of said subdural drainage device and said deformable member inside said housing, and (ii) an extended position with said elongated element extending through said subdural drainage device such that said deformable member automatically extends to an extended, deformed position in which blockages are disrupted in the subdural drainage device when said housing is moved between said first and second housing configurations; and (c) an external drain opening in fluid communication with said housing.

In some embodiments, the housing comprises a rigid telescoping housing.

In some embodiments, the housing comprises a biasing member positioned to maintain said enclosed housing in one of said first and second configurations.

In some embodiments, a method for draining the subdural space, includes positioning a subdural drainage system on a patient. The subdural drainage system includes (a) a subdural drainage device having an opening formed therethrough, said subdural drainage device having an upper portion, a body portion, and a lower portion; (b) a housing having an upper portion and lower portion, with said housing connected to said subdural drainage device; said housing movable between (i) a first configuration and (ii) a second configuration; and (c) an elongated element positioned inside said housing, said elongated element having an upper portion and a lower portion and configured such that said elongated element is moved between (i) a withdrawn position with said elongated element withdrawn from a portion of said subdural evacuation port device, and (ii) an extended position with said elongated element extending through said subdural drainage, wherein said elongated element comprises a deformable member on the lower portion thereof; and (d) an external drain opening formed on either said subdural drainage device or said housing; and moving said housing between said first and second housing configurations so that said elongated element is moved between said withdrawn position with said elongated element withdrawn from a portion of said subdural evacuation port device, and said extended position with said elongated element extending through said subdural drainage device, such that said deformable member automatically extends to an extended, deformed position in which blockages are disrupted in the subdural drainage device when said housing is moved between said first and second housing configurations.

The present invention is explained in greater detail in the drawings herein and the specification set forth below. All United States patent references cited herein are to be incorporated by reference herein in their entirety.

BRIEF DESCRIPTION OF THE DRAWINGS

FIGS. 5A-5C are side cut away views illustrating a subdural drainage system according to some embodiment of the present invention utilizing a locking groove.

FIGS. 8A-8B are side cut away views of a subdural drainage system with a housing in an extended position (FIG. 8A) and a collapsed position (FIG. 8B) according to some embodiments of the invention in which the housing is spring loaded.

FIGS. 11A-11B are side cut away views of a subdural drainage system with a catheter in a retracted position (FIG. 11A) and an extended position (FIG. 11B) according to some embodiments of the invention in which the catheter includes a shape memory deformable member attached thereto.

FIG. 13 is a side view of a blockage/occlusion reduction device according to some embodiments that may be used with the subdural drainage device of FIG. 12.

FIG. 14 is a drug delivery device according to some embodiments that may be used with the subdural drainage device of FIG. 12.

FIG. 17A-17C are the subdural drainage device of FIG. 12 in a use environment with the drug delivery device of FIG. 14.

DETAILED DESCRIPTION OF EMBODIMENTS OF THE INVENTION

Figure 1A:
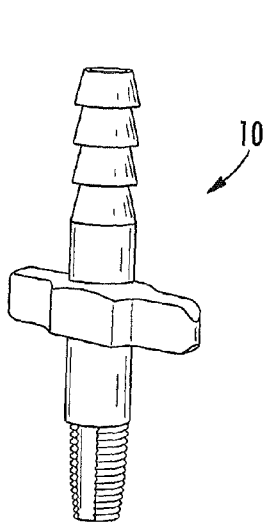
FIG. 1A (Comparative) is a subdural evacuating port system (SEPS) device.
Figure 1B:
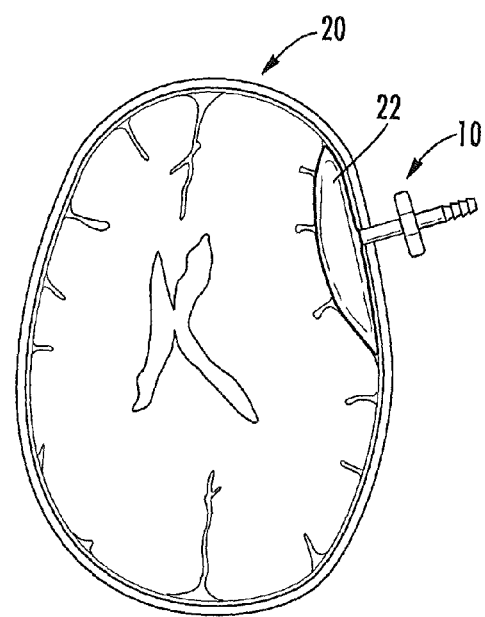
FIG. 1B (Comparative) is the subdural evacuation port system (SEPS) device of FIG. 1A positioned such that a threaded portion thereof is twisted into the skull and the notched ended is attached to silastic tubing connected to a self-suction bulb.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should, be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

In some embodiments, a sealed housing with a movable stylet therein may be connected to a subdural drainage device. The housing may have two configurations, such as an extended configuration and a collapsed configuration, so that the stylet is in a withdrawn position (i.e., withdrawn from at least a portion of the subdural evacuation port) when the housing is in the extended configuration and the stylet is in an extended position extending though the at least a portion of the subdural drainage device when the housing is in the collapsed configuration. As described herein, when the stylet moves with respect to the subdural drainage device (such as between a withdrawn and extended position), the stylet may disrupt blockages formed in the subdural drainage device.

Thus, the sealed housing may provide a sealed enclosure when the catheter or subdural drainage device is in position on a subject patient. Obstructions may be cleared without requiring removal of a subdural catheter or subdural drainage device.

According to some embodiments of the present invention, the subdural drainage device comprises a catheter that may be provided in the sealed housing together with the stylet. The stylet is moved between a withdrawn position (i.e., withdrawn from at least a portion of the catheter) and an extended position extending though the subdural catheter when the housing is moved between the two housing configurations. As described herein, when the stylet is in the extended position, the stylet may engage and/or deform the catheter distal end to disrupt blockages therein. In some embodiments, a catheter support may be provided on a distal end of the housing for securing the housing/catheter in position on a subject patient.

Figure 2B:
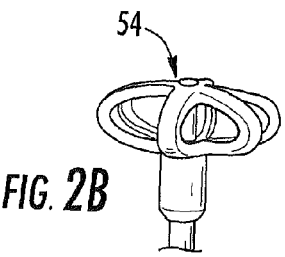
FIGS. 2B-2C (Comparative) are perspective views of the distal end of the catheter of FIG. 2A illustrating the expandable "mushroom-shaped" head with multiple apertures which may be deformed from a flattened or relaxed configuration as shown in FIG. 2B to an extended or stretched position as shown in FIG. 2C by deploying a stylet through the catheter to clear obstruction of the system.
Figure 2C:
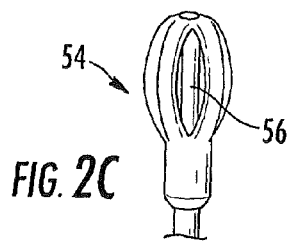
Figure 2A:
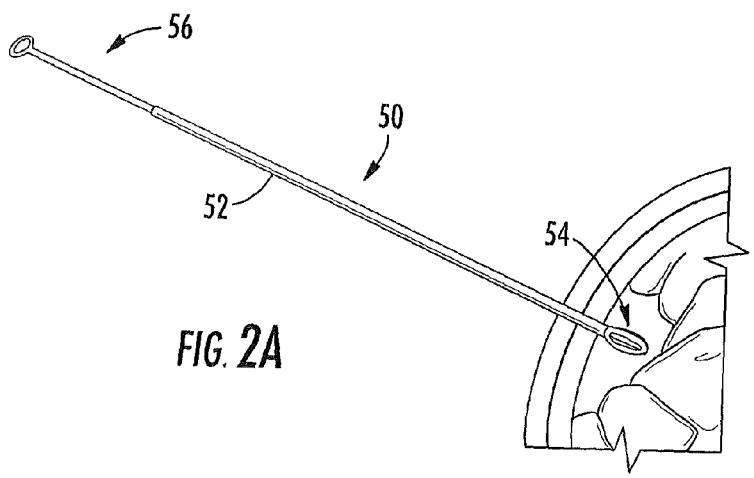

As illustrated in FIGS. 2A-2C, a subdural drainage device, such as a subdural catheter 50 (e.g., Integra, Plainsboro, N.J.), includes a catheter body 52 and a "mushroom-shaped" distal end 54. A stylet 56 may be inserted through the catheter body 52 to move the distal end from a flattened or relaxed configuration as shown in FIG. 2B to an extended or stretched position as shown in FIG. 2C. In this configuration, deformation of the distal end 54 may to allow for clearance of obstructions within the catheter as well as the subdural space.

Figure 3:
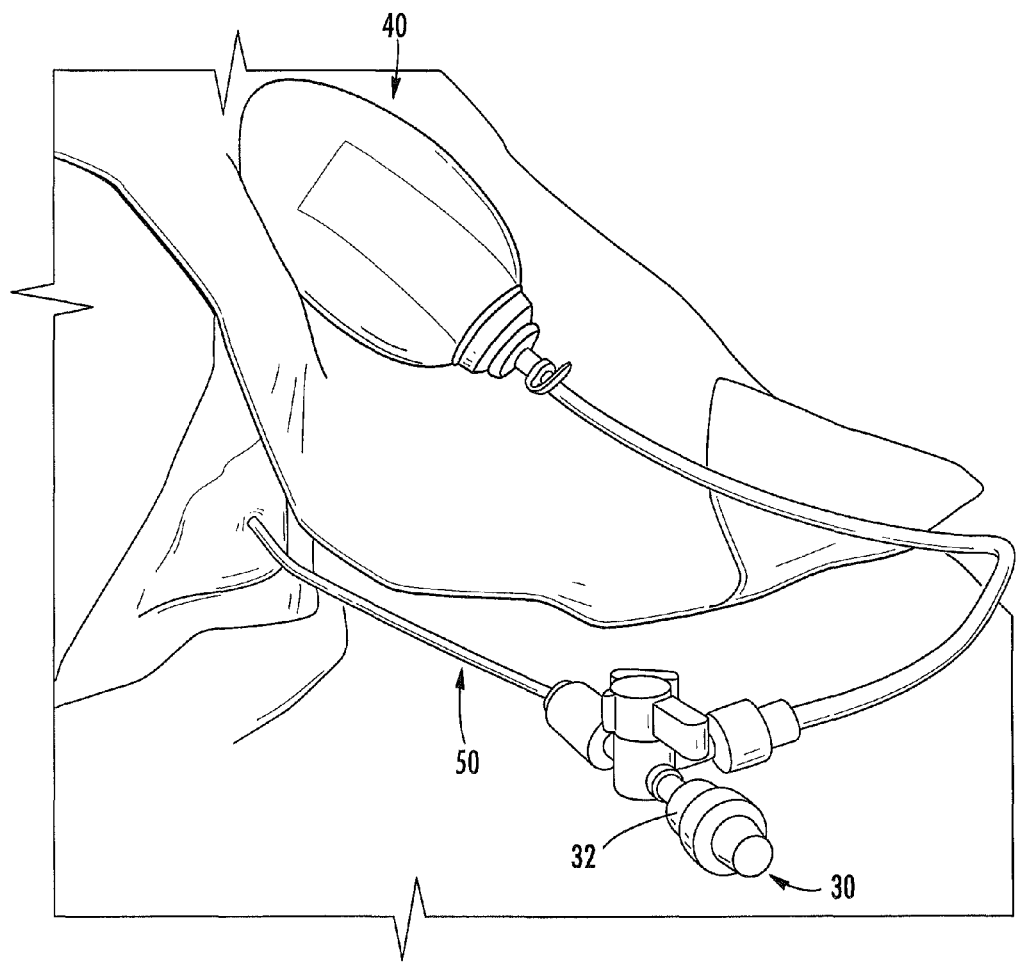
FIG. 3 is a digital photograph of a subdural drainage system according to some embodiments of the present invention in which a three-way stopcock allows for inline access to the subdural catheter for deployment of the stylet to clear obstruction from the system.

As shown in FIG. 3, the subdural catheter 50 is connected to a three-way stopcock 30 and a self-suction bulb 40. The stopcock 30 can include at least one inline port 32, which can be accessed to deploy the stylet 56 through the subdural catheter body 52 in order to clear occlusion within the catheter 50 and/or to deform the catheter distal end 54 as well as dislodge obstructions within the subdural space. Thus, in some embodiments, the catheter distal end 54 may be deformed by a stylet 56 so as to dislodge or reduce clots and other obstructions that may form in the catheter distal end 54 and/or body 52. Accordingly, the need for removing the catheter 50 to clear obstructions is reduced, which may improve the quality of patient care. In some embodiments, the catheter 50 and stylet 56 may be enclosed in a sterile, sealed housing such that clotting and/or obstructions in the catheter may be reduced without compromising the sterility of the catheter 50. Moreover, secondary neurosurgical interventions may be reduced, and consequently, additional procedures, including more invasive surgery performed under general anesthesia, may be reduced. The drainage systems and catheters disclosed herein may further reduce intensive care unit (ICU) and hospital stays, and reduce the overall financial burden of treatment for this often difficult pathology in a typically elderly population with multiple coexisting medical conditions. The system of FIG. 3 has been used in two patients (ages 75 and 89) with positive results. The ability to safely re-establish flow for the drainage of subacute and chronic subdural fluid collections following initial obstruction of the system has been successfully demonstrated (both clinically and radiographically). It is believed that, without the features of this system, the patients likely would have required additional operative intervention to adequately evacuate the hematomas and decompress the cerebrum to relieve the persistent neurologic deficit.

Figure 4A:
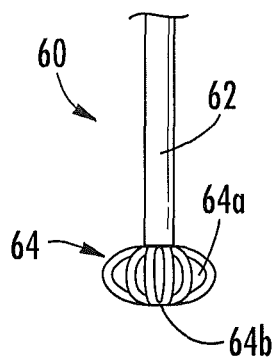
FIGS. 4A-4D are side cut away views illustrating various configurations of catheter distal end portions according to some embodiments of the present invention.
Figure 4B:
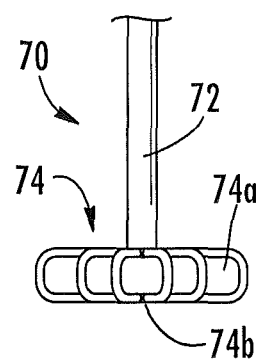
Figure 4C:
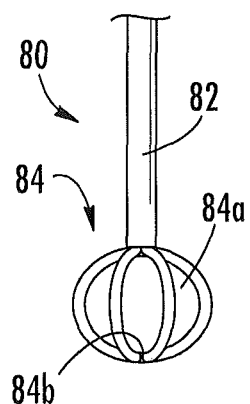
Figure 4D:
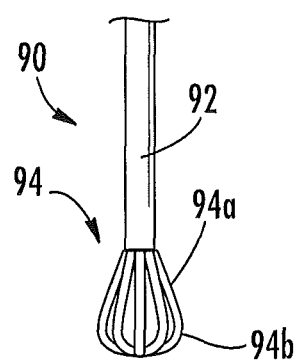

The catheter distal end may take any of a variety of configurations, including but not limited to the configurations illustrated in FIG. 4A-4D. In particular, FIG. 4A illustrates a catheter 60 with a catheter body 62 and a generally mushroom-shaped distal end 64. FIG. 4B illustrates a catheter 70 with a catheter body 72 and a generally wheel-shaped distal end 74. FIG. 4C illustrates a catheter 80 with a catheter body 82 and a generally spherical-shaped distal end 84. FIG. 4D illustrates a catheter 90 with a catheter body 92 and a generally pear-shaped distal end 94. Accordingly, any suitable shape may be used including mushroom-shaped, spherical-shaped, oval-shaped, pear-shaped, wheel-shaped, radial shaped, kidney-shaped, etc. In some embodiments, the distal ends 64, 74, 84, 94 include one or more drain openings or fenestrations 64a, 74a, 84a, 94a therein for draining the subdural space. The distal end 64, 74, 84, 94 is typically deformable, by action of the stylet discussed below, and configured so that deformation of the distal end 64, 74, 84, 94 deforms the openings or fenestrations 64a, 74a, 84a, 94a, and/or the drain lumen therein, so that occlusions therein may be broken or dislodged by deformation of the distal end 64, 74, 84, 94 with the stylet, as described herein. However, in some embodiments, the catheter distal end may be a simple lumen open end with the fenestrations 64a, 74a, 84a, 94a omitted.

The distal ends 64, 74, 84, 94 may be configured with a bumper portion or stopper 64b, 74b, 84b, 94b against which the distal tip of the stylet can abut and press against to deform the distal end of the catheter. The distal ends 64, 74, 84, 94 of the catheter 60, 70, 80, 90 may be configured to engage, enclose or contain the stylet, with the bumper portions 64b, 74b, 84b, 94b blocking the stylet tip from directly contacting underlying brain tissue, serving to reduce the possibility of damage to underlying brain tissue by direct contact with the stylet.

Although the catheter distal ends 64, 74, 84, 94 are illustrated with respect to bumper portions 64b, 74b, 84b, 94b for containing the stylet, it should be understood that the stylet may be adhered to or mounted on a portion of a catheter distal end, such as distal ends 64, 74, 84, 94, such that the stylet may be positioned through a catheter body throughout a surgical procedure. The stylet may be mounted to the catheters 60, 70, 80, 90 at various points including the distal ends 64, 74, 84, 94, the opposite proximal ends of the catheters 60, 70, 80, 90, the housing or combinations thereof.

In some embodiments, a deformable member may be positioned on a distal end portion of an elongated element, such as a subdural catheter or stylet, and the housing of the device may be configured to hold the elongated element and deformable member for positioning in the subdural drainage device during a surgical procedure. The deformable member may be formed of a shape memory material such that the deformable member automatically changes shape when the catheter or stylet extends out of the housing. Any suitable shape memory material may be used, including shape memory alloys such as nitinol, shape memory polymers, and composites thereof (with other shape memory or non-shape memory materials to form a shape-memory composite material or structure). See, e.g., U.S. Pat. Nos. 8,328,842 and 7,879,004; C. Ykacki et al., Unconstrained Recovery Characterization of Shape-Memory Polymer Networks for Cardiovascular Applications, Biomaterials 28, 2255-2263 (2007); see generally K. Otsuka and C. Wayman, Shape Memory Materials (Cambridge University Press 1999).

As illustrated in FIGS. 11A-11B, a subdural drainage system 600 includes a housing 610 having an upper portion and a subdural drainage device or port 630. The housing 610 includes a drainage opening 618, a lower end 619, an elongated member 620, telescoping members 622 and a biasing member, such as spring 624. The elongated element 620 includes a deformable member 621 on a distal end thereof. The subdural drainage port 650 includes an upper portion that connects to or is integrally formed with the housing 610. The lower portion 619 is configured to connect to the skull of a subject. However, the lower portion 619 may be configured to connect with a separate drainage port.

The spring 624 biases the elongated element 620 in the withdrawn position as shown in FIG. 11A. When the telescoping member 622 is pressed, the elongated element 620 extends through the subdural drainage port 650 as shown in FIG. 11B. The deformable member 621 automatically deforms as shown in FIG. 11B and removes or reduces any clots and/or obstructions.

It should be understood that various dimensions and/or relative proportions of the system may be modified. For example, although the housing 610 is illustrated as a telescoping housing, it should be understood that other configurations may be used to move the stylet 620, including reduced profile configurations. In some embodiments, the elongated element 620 may be hollow to permit continuous flow and/or drainage via the housing 610.

Shape memory materials that may be used for the deformable member 621 include biocompatible shape memory polymers, metals or alloys.

Figure 12:
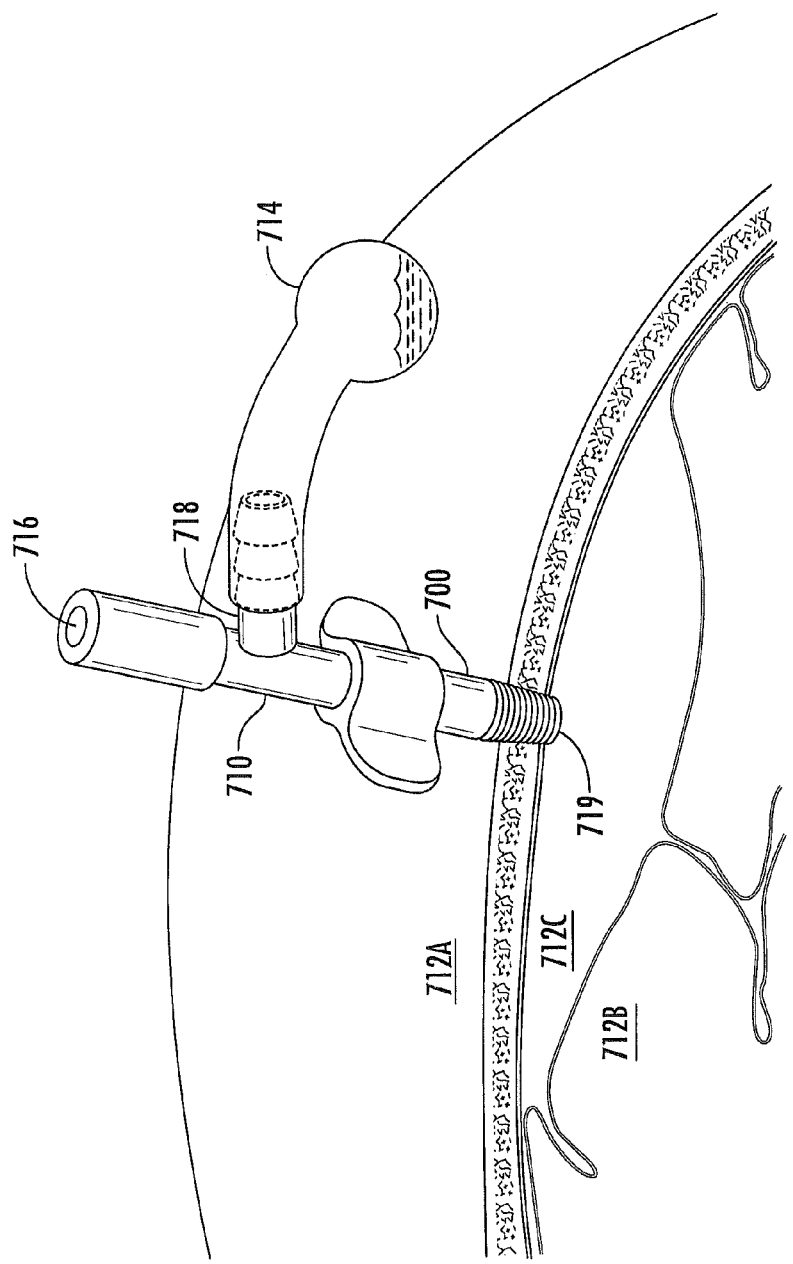
FIG. 12 is a side cut away view of a subdural drainage device according to some embodiments.

In some embodiments, a subdural drainage system may be provided that includes a port into which an occlusion device (such as an elongated element with a deformable member attached thereto) or other medical devices may be removably inserted. As illustrated in FIG. 12, a subdural drainage device 700 includes a housing 710 and a drain opening 718 that is connected to a drain reservoir 714. The housing 710 includes a lower opening 719 that is configured to be secured on a skull 712A of a patient for drainage of the subdural area 712C adjacent the brain 712B, for example, using self-tapping threads. The housing 710 includes an upper opening 716 through which an occlusion stylet or catheter or other suitable medical instruments may be inserted.

Although the housing 710 may be used to provide an entry access portal for any suitable medical device, examples of medical devices that may be inserted in the housing 710 include a deformable blockage catheter 800 as shown in FIG. 13 and a drug delivery device 900 as shown in FIG. 14. As shown in FIG. 13, a deformable blockage-removal device 800 includes a housing 810 having a handle 820 at an upper end that is connected to an elongated element or catheter 830. A biasing member or spring 840 is in the housing 810 and a deformable member 850 is connected to the distal end of the catheter 830. As shown in FIG. 14, the drug delivery device 900 includes a support 910, an upper portion 920 that includes an opening 922 that is configured to attach to a drug reservoir or drug delivery control device. A lever 930 is attached to an internal valve (not shown) for turning the drug delivery on or off. The drug delivery device 900 further includes a catheter 940 that is configured to be inserted through the skull of a patient for direct delivery of a drug or other therapeutic agent. Any suitable drug or therapeutic agent may be used, including thrombolytic agents, antibiotic agents, and/or chemotherapy agents. In addition, the drug delivery catheter 940 may include side ports or apertures on a side and/or bottom portion thereof to facilitate the dispersing of the drug or therapeutic agent in the patient.

Figure 15:
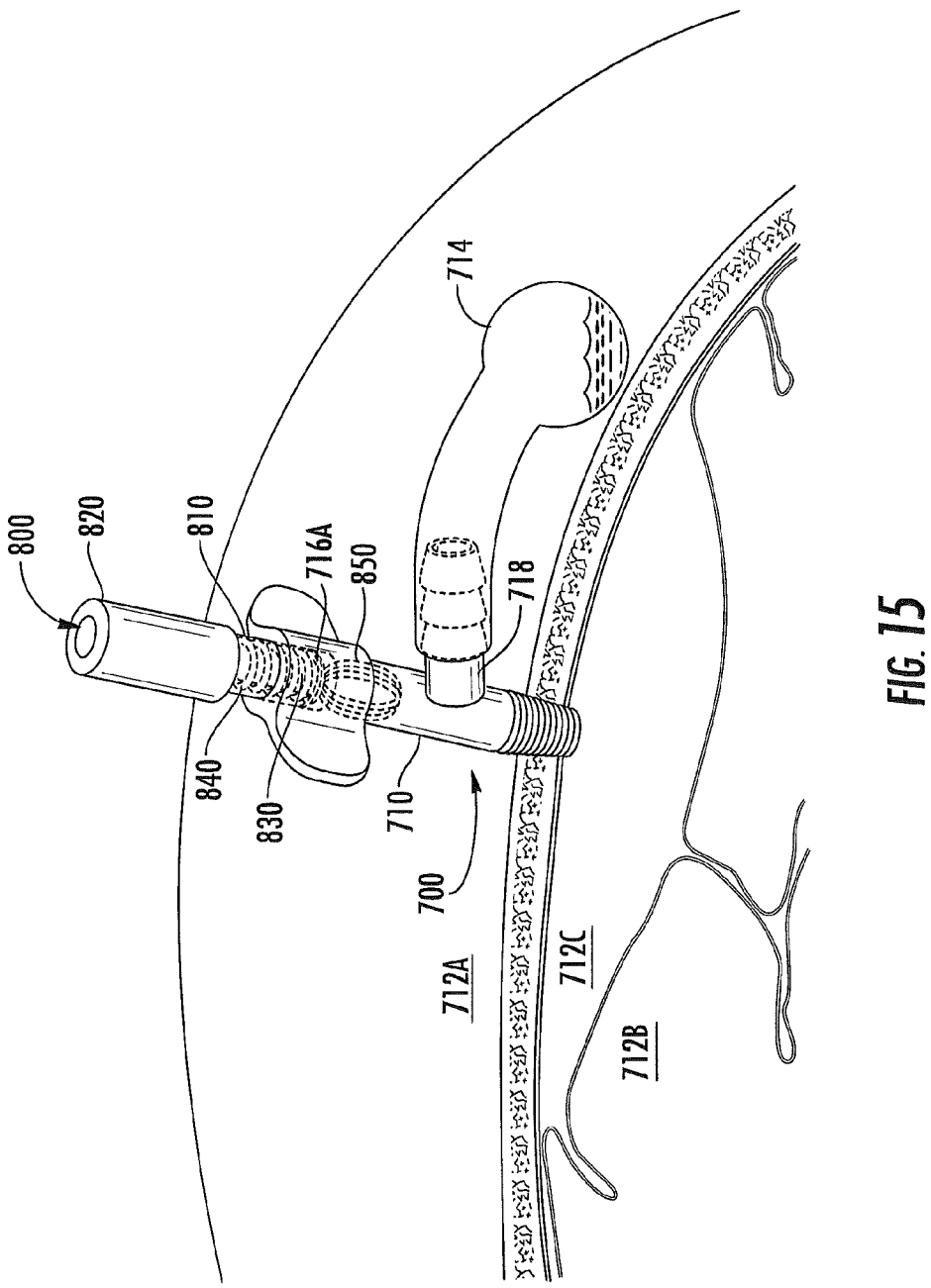
FIG. 15 is the subdural drainage device of FIG. 12 in a use environment with the blockage/occlusion reduction device of FIG. 13 in a retracted position.
Figure 16:
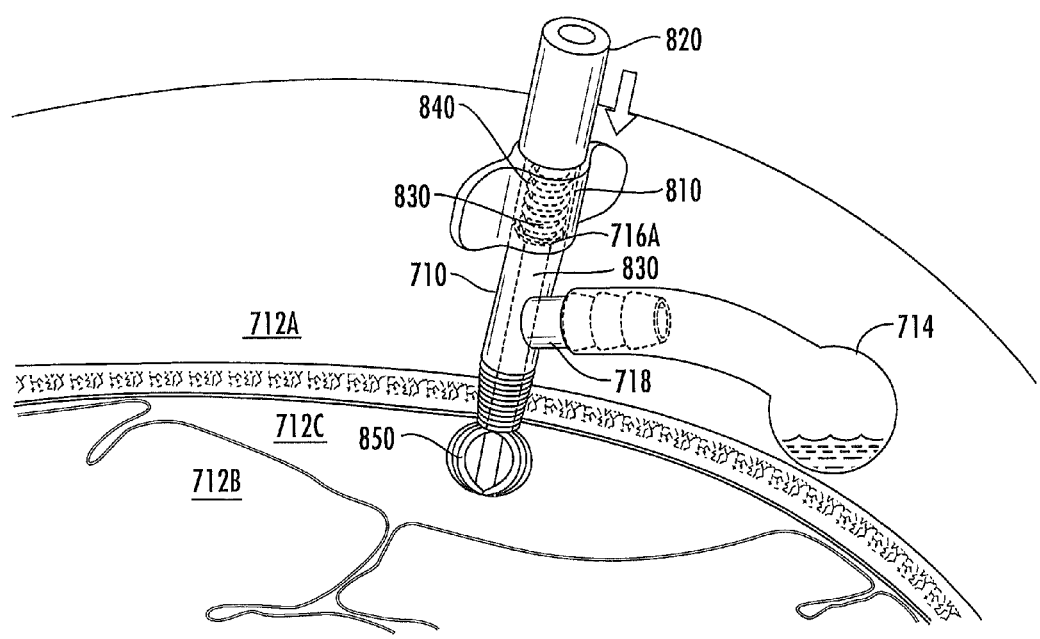
FIG. 16 is the subdural drainage device of FIG. 12 in a use environment with the blockage/occlusion reduction device of FIG. 13 in an extended position.

As shown in FIGS. 15-16, the deformable blockage-removal catheter device 800 may be inserted into the housing 710 of the subdural drainage device 700. The housing 810 of the catheter device 800 forms a telescoping housing together with the housing 710 of the drainage device 700. As illustrated in FIG. 15, the housing 710 includes an internal ledge 716A, and housing 810 rests against the ledge 716A so that the spring 840 biases the catheter 830 in an extended position in which that deformable member 850 is positioned in the housing 710 in a first or compacted configuration. When the handle 820 is depressed as shown in FIG. 16, the catheter 830 moves with respect to the housing 810 and extends into the skull and the deformable member 850 exits the housing 710 and automatically deforms into a second or relaxed configuration in which the deformable member 850 deforms to reduce or remove occlusions. As illustrated, in the relaxed, extended configuration shown in FIG. 16, the deformable member 850 has a diameter that is greater than the diameter of the housing 710. However, when the handle 820 is released or retracted, the deformable member 850 is withdrawn into the housing 710 and is moved to the first or compacted configuration of FIG. 15. In this configuration, the catheter device 800 may be removably inserted into the drainage device 700 for occlusion reduction/removal operations, e.g., on an as-needed basis.

Figure 17A:
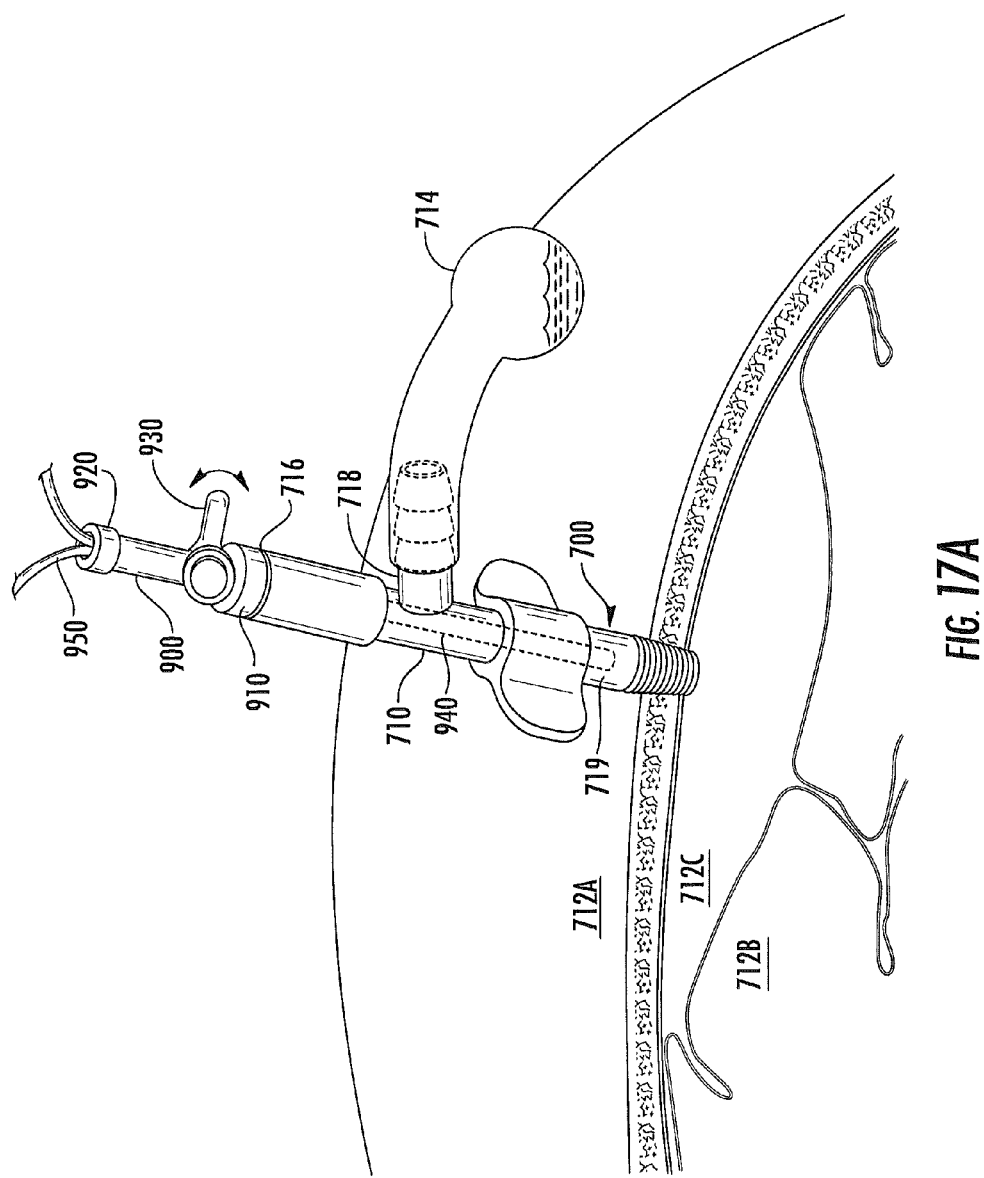
Figure 17C:
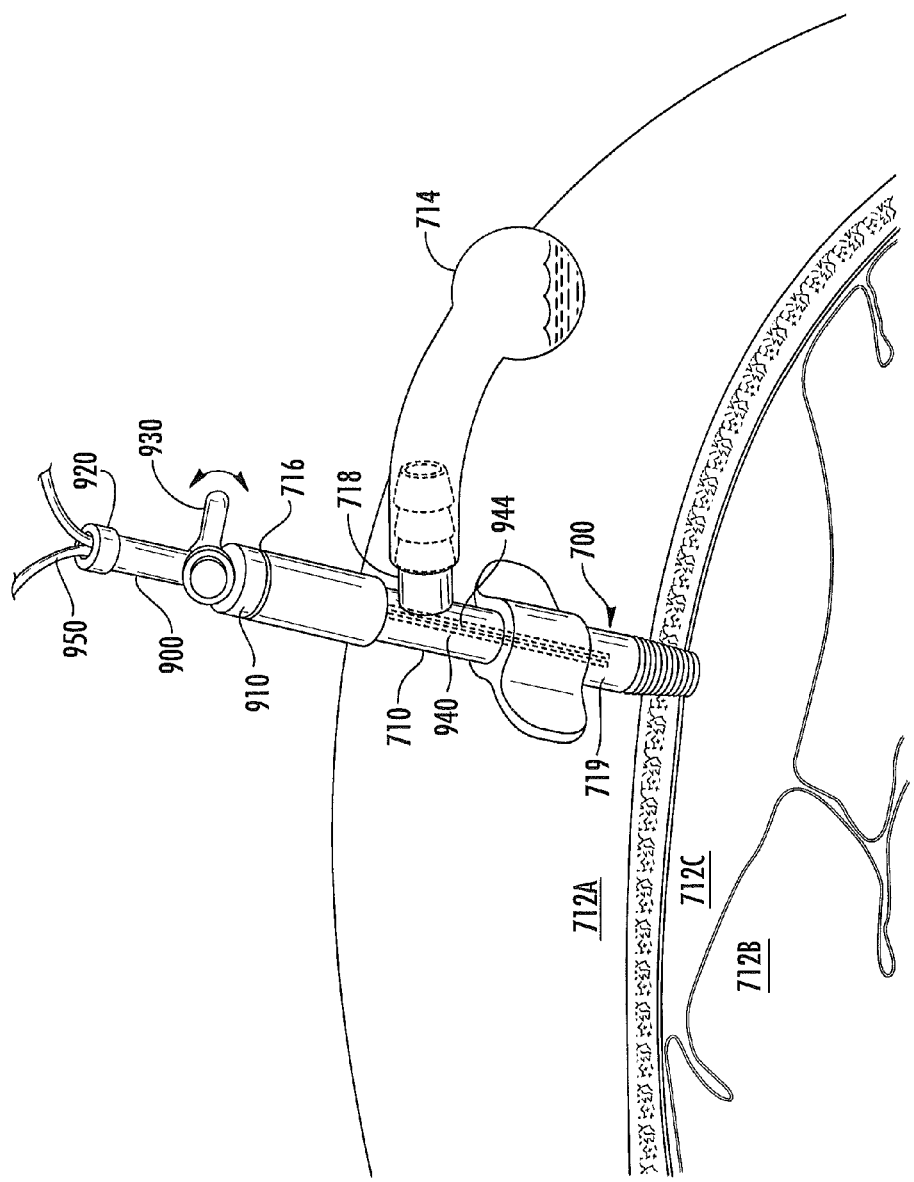

As shown in FIGS. 17A-17C, the drug delivery device 900 may be inserted into the skull 712A via the drainage device 700. As shown, the drug delivery catheter 940 is secured by the support 910 and extends through the housing 710. The delivery device 900 is further connected to a conduit 950 that; in turn, connects to a drug reservoir. As illustrated in FIG. 17A, the drug or therapeutic agent may exit the device 900 from an aperture in the distal end of the catheter 940. As shown in FIG. 17B-17C, apertures 942 (FIG. 17B) or side ports 944 (FIG. 17C) may be provided to facilitate more even dispersing of the drug or therapeutic agent into the patient.

In this configuration, the subdural drainage device 700 may be surgically implanted in the skull 712A as illustrated for generally continuous drainage operations while different instruments may be removably inserted therein as desired, e.g., to remove or reduces any clots and/or obstructions with the catheter device 800 or to deliver a drug via the drug delivery device 900. Although embodiments according to the invention are illustrated with the catheter 940 positioned above the subdural region 712C, it should be understood that any suitable length could be used, including catheters 940 that extend into or adjacent the skull 712A or subdural region 712C.

Figure 18:
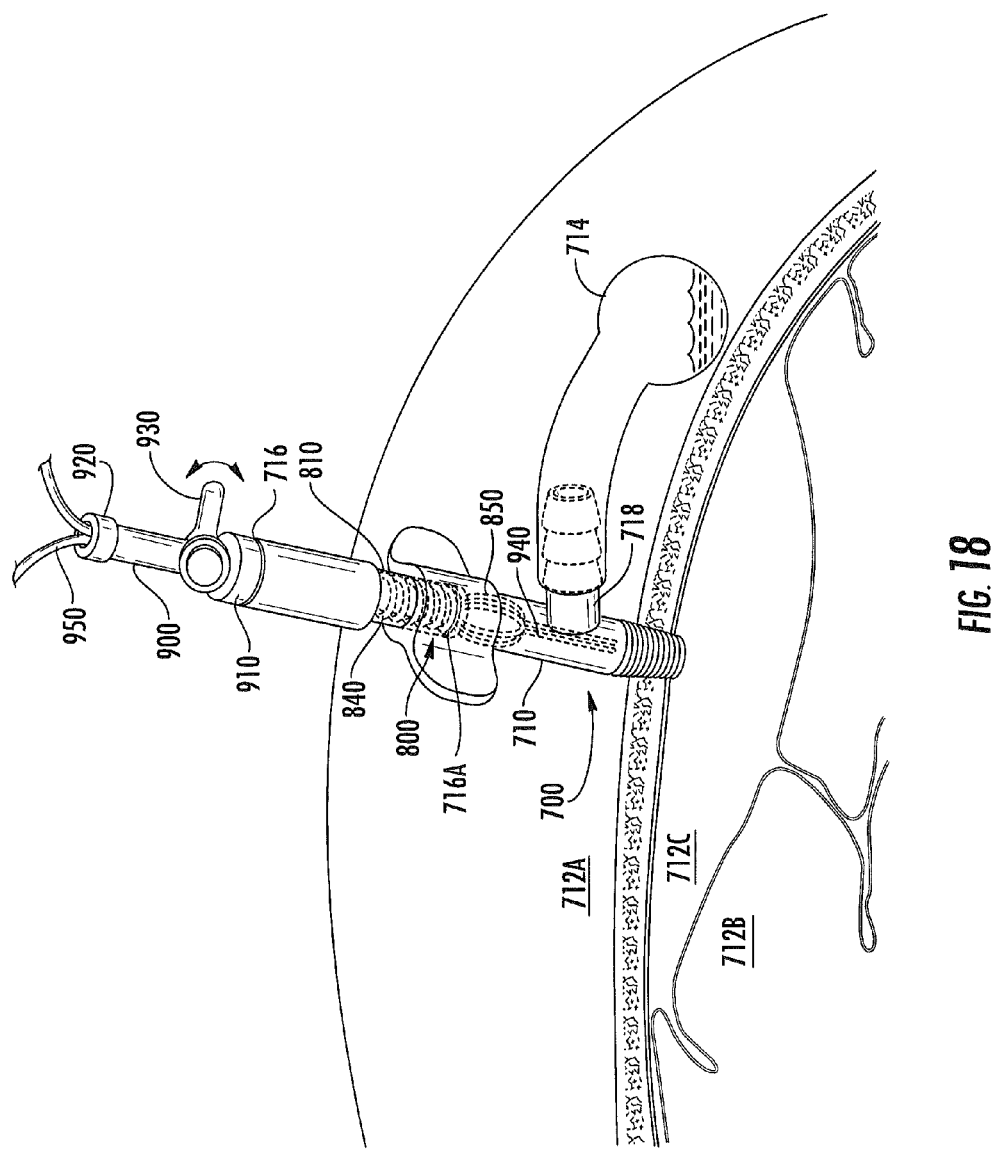
FIG. 18 is the subdural drainage device of FIG. 12 in a use environment with the blockage/occlusion reduction device of FIG. 13 in a retracted position and the drug delivery device of FIG. 14.
Figure 19:
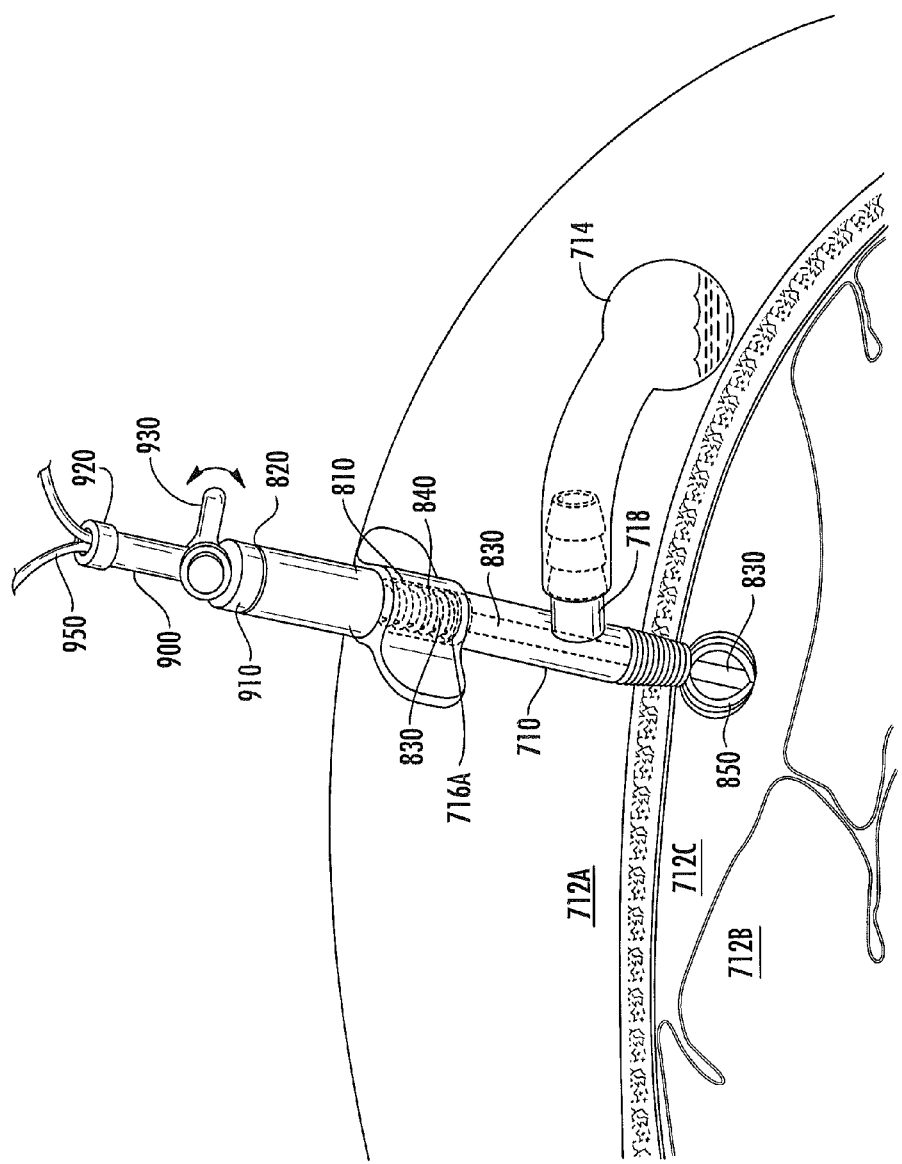
FIG. 19 is the subdural drainage device of FIG. 12 in a use environment with the blockage/occlusion reduction device of FIG. 13 in an extended position and the drug delivery device of FIG. 14.

As illustrated in FIGS. 18-19, in some configurations, the subdural drainage device 700 may be configured to accept two or more devices at the same time. As shown, the catheter occlusion/drainage device 800 includes a central opening through the catheter 830 into which the drug delivery device 900 and the drug deliver catheter 940 is positioned. In this configuration, the deformable member 850 and the drug delivery device 900 may be concurrently positioned in the patient for simultaneous delivery of a drug or other therapeutic agent and the reduction of occlusions. As illustrated, the occlusion device catheter 830 moves between a retracted position (FIG. 18) and an extended position (FIG. 19) without substantially disturbing the drug delivery device 900.

The present invention is described in greater detail in the following non-limiting Examples.

Example 1

Stylet Housing with Telescoping Body

As illustrated in FIGS. 5A-5C, a subdural drainage system 100 includes a telescoping housing 110 and a subdural drainage device or catheter 150 in the housing 110. The housing 110 has two telescoping members 112, 114, a channel lock 116, a drain opening 118 and a lower opening 119. A stylet 120 is enclosed by the housing 110 and attached to a handle member 122.

The lower opening 119 may be configured to be secured on a skull of a subject, or as shown in FIG. 5B, a catheter support 130 having an upper portion 132 connected to the housing lower opening 119 and a lower portion 134 may be used. The catheter support lower portion 134 is configured to be secured in a skull of a subject.

As illustrated, housing 110 is movable between an extended configuration (FIGS. 5A-5B) and a collapsed configuration (FIG. 5C). In the extended configuration shown in FIGS. 5A-5B, the stylet 120 is withdrawn from at least a portion of the catheter 150. In the collapsed configuration shown in FIG. 5C, the stylet 120 extends through the catheter, engages the catheter distal end 154, and deforms the distal end 154 to dislodge obstructions and/or reduce clotting.

As illustrated, the channel lock 116 of the stylet housing 110 is an L-shaped channel formed in the lower housing member 114. The stylet 120 has a tab protruding therefrom that is contained but travels within the channel lock 116. Rotation of the handle member 122 rotates the stylet 120 from a locked to unlocked position by moving the tab from the horizontal to vertical portion of the channel lock 116 and permits the telescoping housing members 112, 114 to collapse, extending the stylet 120 into the catheter 150 and deforming the catheter distal end 154. Note that, while the stylet 120 is shown positioned entirely outside the catheter when the housing 110 is in its extended position, the stylet 120 could be contained within the catheter 150 when in the extended position, so long as components are appropriately dimensioned so that collapsing of the housing 110 effectively deforms the catheter distal end 154. Moreover, the channel lock 116 may be omitted and/or other locking configurations can be used. In some embodiments, a locking mechanism may be used to substantially prevent the stylet 120 from extending into the subdural space. For example, the channel lock 116 may be sized and configured such that the stylet 120 is held in position by the channel lock 116 such that the stylet is substantially prevented from extending beyond the catheter 150 and/or into the subdural space.

Figure 6:
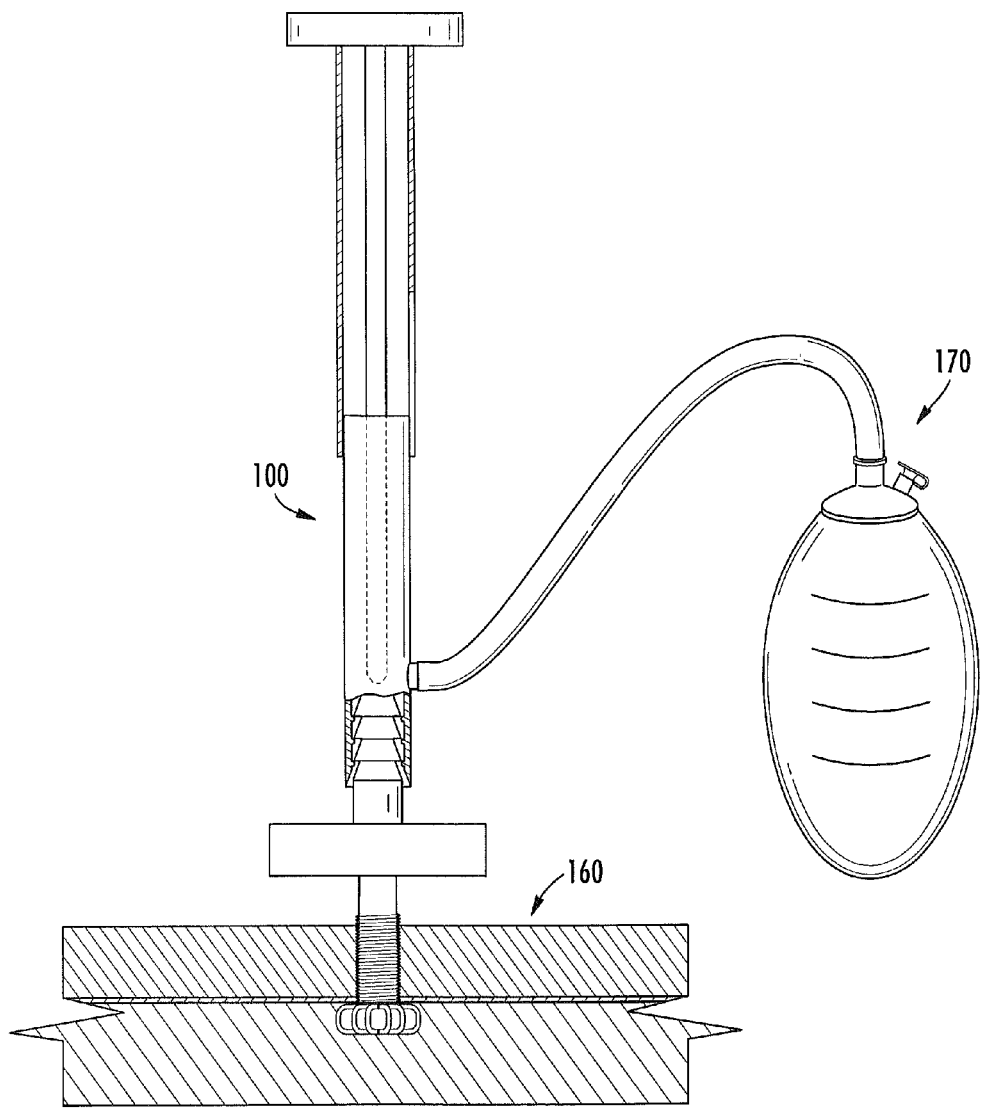
FIG. 6 is a schematic illustration of drainage system of FIG. 5 as placed on a subject.

FIG. 6 shows the system 100 installed on the skull 160 of a subject, with a bulb suction device 170 attached to the external drain 118 to serve as a drain reservoir.

Example 2

Stylet Housing formed from Flexible Polymer

Figure 7A:
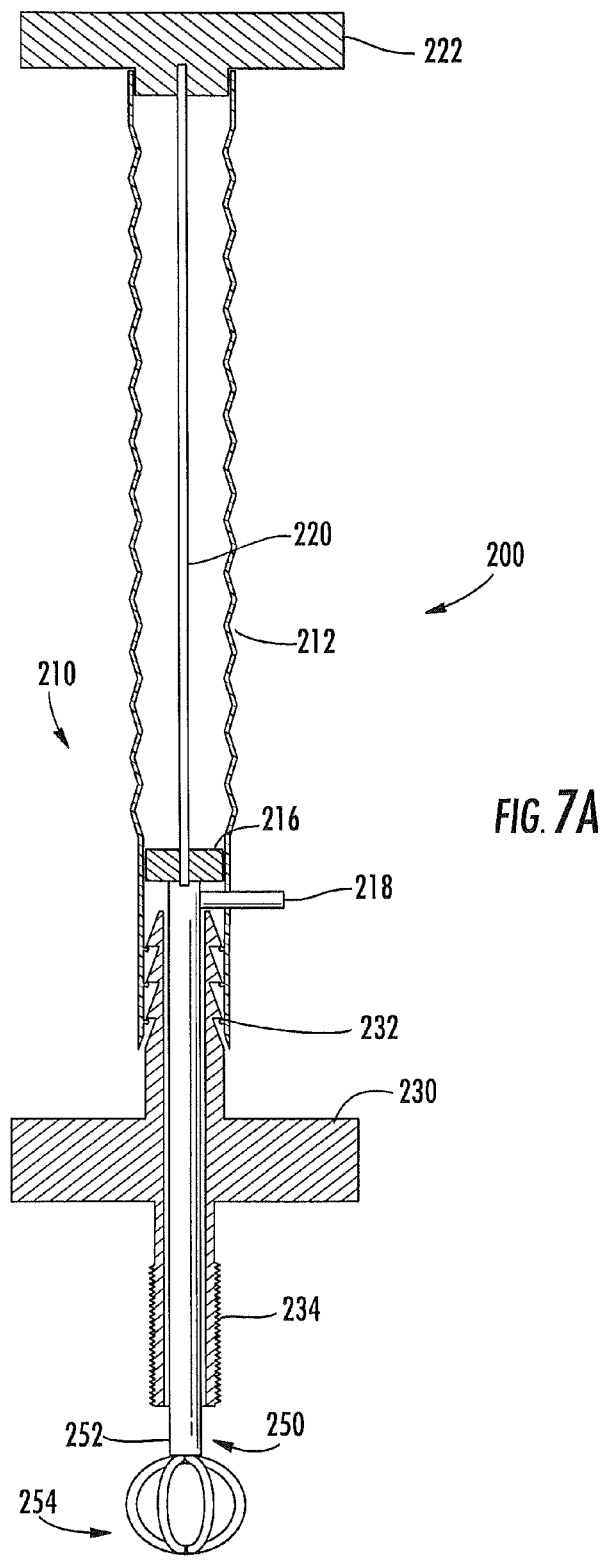
FIGS. 7A-7B are side cut away views of a subdural drainage system with a housing in an extended position (FIG. 7A) and a collapsed position (FIG. 7B) according to some embodiments of the present invention in which the housing is formed of flexible tube.
Figure 7B:
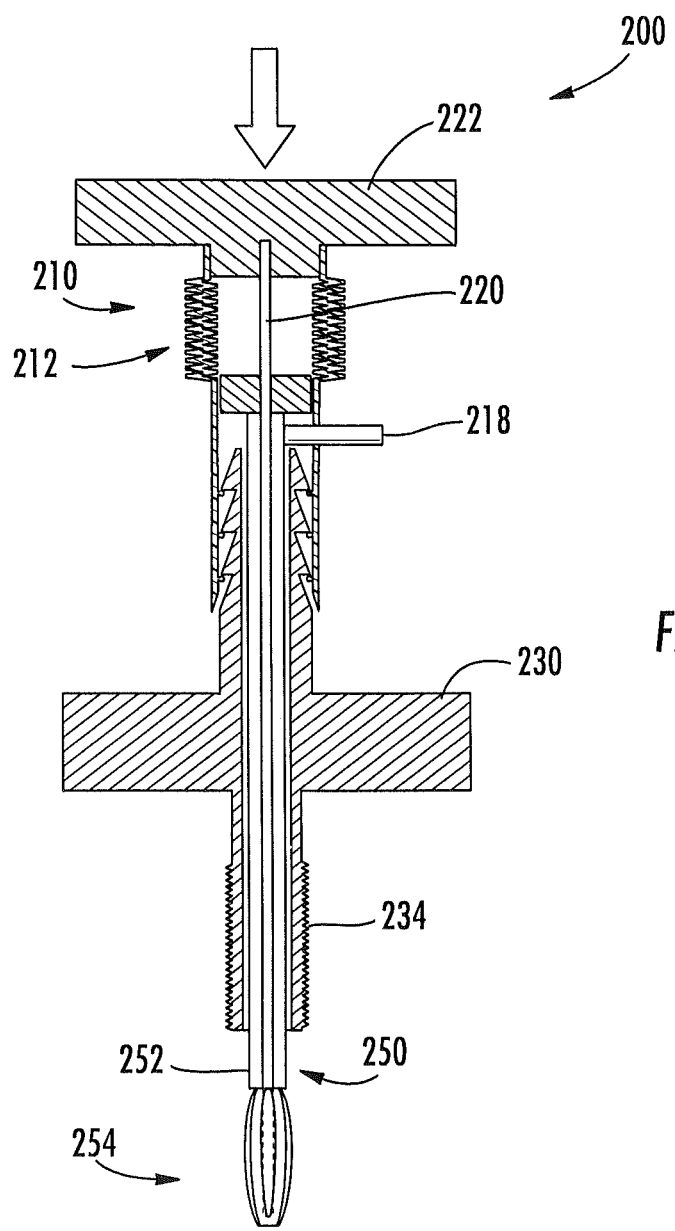

As illustrated in FIGS. 7A-7B, a subdural drainage system 200 includes a housing 210 that encloses a stylet 220. The housing 210 includes a collapsible tubular member 212, a stopper 216, a drain opening 218, a handle 222 and a catheter support 230. The collapsible member 212 is connected to the catheter support 230 at a threaded upper portion 232 of the catheter support 230. A lower portion 234 of the catheter support 230 is configured to be secured in the skull of a subject. A subdural drainage device, such a catheter 250, has a catheter body 252 and a distal end 254 that is positioned in the catheter support 234 such that the catheter distal end 254 extends away from the lower portion 234 of the catheter support 230.

As illustrated, the collapsible tubular member 212 is movable between an extended configuration (FIG. 7A) in which the stylet 220 is withdrawn from at least a portion of the catheter 250 and a collapsed configuration (FIG. 7B) in which the stylet 220 extends through the catheter 250 to engage the distal end 254 to deform the distal end 254 and dislodge obstructions and/or reduce clotting.

The collapsible tubular member 212 as illustrated is accordion-pleated. However, any suitable collapsible configuration may be used. In some embodiments, the tubular member 212 is formed of a flexible material, such as flexible silicone tubing. A conventional tube clamp (not shown) may optionally be provided outside and around the tube to lock the stylet in place by "pinching" the stylet. Alternatively, the tube can be biased in the extended position and/or spring-loaded. Although the stylet 220 is shown in FIG. 7A as being generally withdrawn from the catheter 250 in FIG. 7A, it should be understood that in some embodiments, the stylet 220 may extend into a portion of or through the entire length of the catheter body 250. In some embodiments, the stylet 220 has a diameter that is sufficiently smaller than the catheter 250 such that fluid may flow from a subdural space, through the catheter, and exit from the catheter drain 218.

Example 3

Housing with Internal Biasing Member

As illustrated in FIGS. 8A-8B, a subdural drainage system 300 includes a housing 310 and a subdural drainage device or catheter 350 in the housing 310. The catheter includes a body 352 and a deformable distal end 354. The housing 310 encloses a stylet 320. The housing includes a drain opening 318, a lower portion 319, an actuator or button 322 and a biasing member or spring 324. The lower portion 319 may be connected to a connecting member or catheter support (not shown) for providing a connection portal to the skull of a subject or the lower portion 319 may be connected directly to a skull of a subject (e.g., the lower portion 319 may include a threaded portion for connecting to a skull of a subject) to provide fluid communication to the drain opening 318 (which may be in turn connected to a fluid reservoir (not shown)).

The button 322 is biased by the spring 324 in the extended position as shown in FIG. 8A. The button 322 is connected to the stylet 320, and the stylet 320 extends through the catheter body 352 and the distal end 354 when the button 322 is in the extended configuration. When the button 322 is pressed into the housing collapsed configuration as shown in FIG. 8B, the stylet 320 is moved with respect to the catheter 350 such that they stylet 320 engages and/or deforms the catheter distal end 354 as shown in FIG. 8B. In some embodiments, the stylet 316 is connected or adhered to the catheter distal end 354.

Example 4

Housing with Internal Biasing Member

Figure 9A:
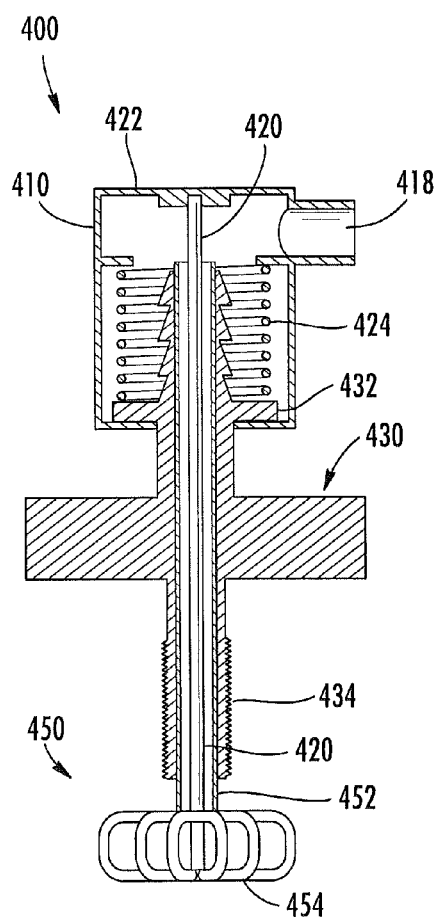
FIGS. 9A-9B are side cut away views of a subdural drainage system with a housing in an extended position (FIG. 9A) and a collapsed position (FIG. 9B) according to some embodiments of the invention in which the housing is spring loaded.
Figure 9B:
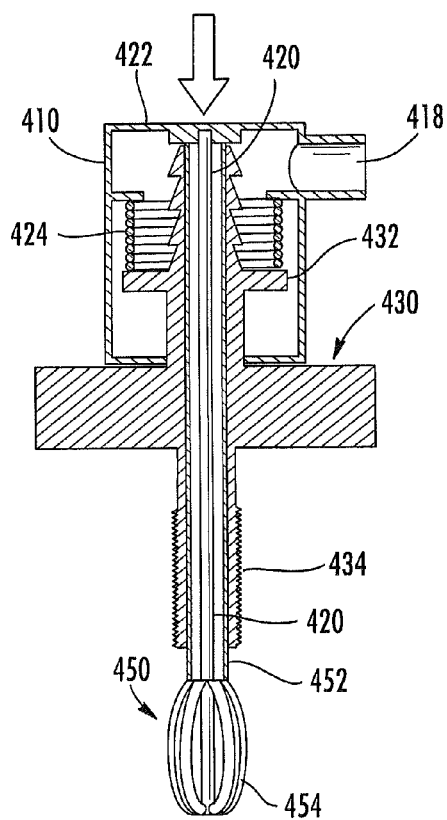

As illustrated in FIGS. 9A-9B, a subdural drainage system 400 includes a housing 410 and a subdural drainage device or catheter 450 in the housing 410. The housing includes an upper portion 412, a stylet 420, a drain opening 418, an actuator button 422, a biasing member or spring 424 and a catheter support 430. The catheter support 430 includes an upper portion that is connected to the housing portion 412 and a lower portion 434 that is configured to be connected to a skull of a subject. The drain opening 418 may be connected to a fluid reservoir. The catheter 450 includes a body 452 and a distal end 454.

The button 422 is connected to the stylet 420, and the spring 424 biases the stylet 420 and button 422 in the extended configuration as shown in FIG. 9A. As shown in FIG. 9B, when the button 422 is compressed or collapsed, the stylet 420 moves to extend through the catheter 450 and deform the catheter distal end 454 to dislodge obstructions and/or reduce clotting.

Example 5

Housing with Stylet

Figure 10A:
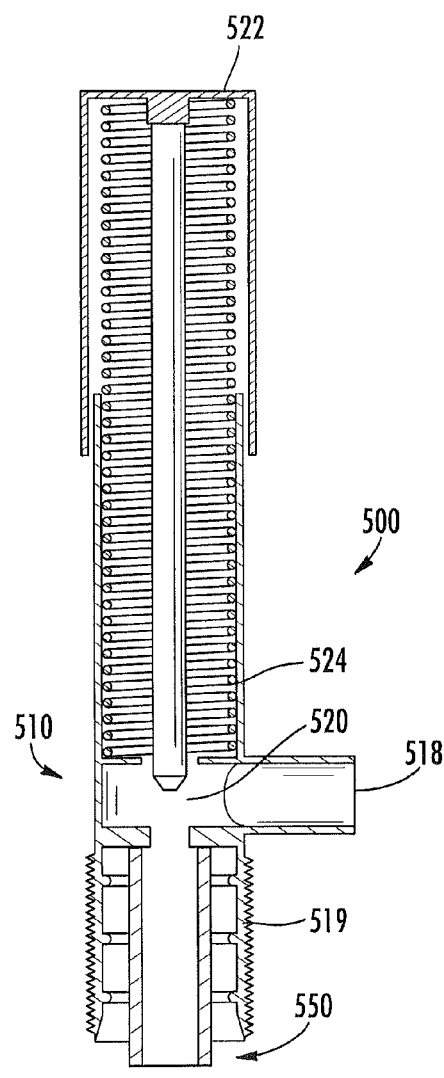
FIGS. 10A-10B are side cut away views of a subdural drainage system with a housing in an extended position (FIG. 10A) and a collapsed position (FIG. 10B) according to some embodiments of the invention in which the stylet is configured to clear obstructions within the drainage port.
Figure 10B:
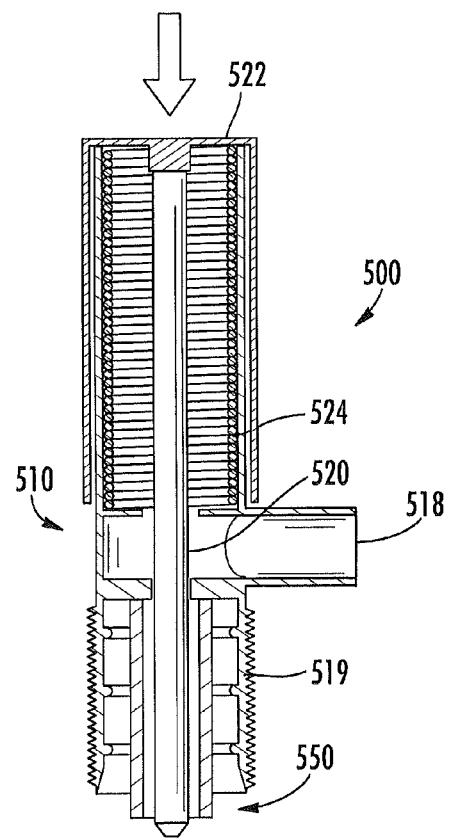

As illustrated in FIGS. 10A-10B, in some embodiments a separate catheter member may be omitted. As illustrated, a subdural drainage system 500 includes a housing 510 having an upper portion and a subdural drainage device or port 530. The housing 510 includes a drainage opening 518, a lower end 519, a stylet 520, telescoping members 522 and a biasing member, such as spring 524. The subdural drainage port 550 includes an upper portion that connects to or is integrally formed with the housing 510. The lower portion 519 is configured to connect to the skull of a subject. However, the lower portion 519 may be configured to connect with a separate drainage port.

The spring 524 biases the stylet 520 in the withdrawn position as shown in FIG. 10A. When the telescoping member 522 is pressed, the stylet 520 extends through the subdural drainage port 550 and removes or reduces any clots and/or obstructions therein. In some embodiments, the diameter of the stylet 520 is sufficiently large such that it extends substantially across the diameter of the interior region of the port 550.

In some embodiments, the interior diameter of the subdural drainage device or port 550 is about 4-5 mm and the diameter of the stylet is slightly smaller, such as about 3.5-4.5 mm, so as to physically remove clotting and/or obstructions in the port 550. However, any suitably sized subdural drainage device and stylet may be used. It should be understood that various dimensions and/or relative proportions of the system may be modified. For example, although the housing 510 is illustrated as a telescoping housing, it should be understood that other configurations may be used to move the stylet 520, including reduced profile configurations.

Numerous variations of the foregoing will be apparent to those skilled in the art. Although embodiments of the invention are illustrated with a housing that is removably engaged to the subdural drainage device (e.g., the catheter, catheter support and/or subdural drainage port), it should be understood that the subdural drainage device and housing may be permanently connected and/or provided as an integrated unit. For example, although the catheter support and housing (e.g., the catheter supports 130, 230 and 430 and the corresponding housing 110, 210 and 410 in FIGS. 5A-5C, FIGS. 7A-7B and FIGS. 9A-9B, respectively) are illustrated as separate members, the catheter support and housing could be integrated and formed as a single unitary member. Moreover, the housings 110, 210, 310, 410 and 510 and drainage ports 118, 218, 318, 418 and 518 may also be formed as a single member. In addition, various configurations may be used to move the stylet, including configurations that may provide a reduced housing profile.

Although the drainage opening is illustrated as a part of the housing (e.g., the drainage openings 118, 218, 318, 418 and 518 in FIGS. 4-10), it should be understood that the drainage opening may be provided on any suitable portion of the subdural drainage system, including the catheter support and/or the subdural evacuation port device.

Although embodiments according to the present invention are described herein with respect to a biasing member (e.g., springs 324, 424 of FIGS. 8A-8B and FIGS. 9A-9B, respectively) that biases the housing (or a portion thereof) in an extended position such that the stylet is withdrawn from at least a portion of the catheter, it should be understood that the spring member may bias the housing in another position, such as a collapsed position. Thus, actuation of the stylet movement between two stylet positions may occur in the reverse order from that shown. In some embodiments, the movement between the positions in either order may be sufficient to dislodge and reduce obstructions.

Embodiments according to the present invention are described herein with respect to a stylet that generally passes through the drainage pathway (such as through the catheter lumen), a stylet lumen may be provided that is not part of the drainage pathway. For example, a stylet lumen may be positioned adjacent the drainage lumen and configured so that movement of the stylet into the stylet lumen deforms a portion of the catheter.

Subdural Drainage Devices and Optional Catheter Supports.

The subdural drainage devices that may be connected to housing/stylets according to some embodiments of the present invention may take any of a variety of forms. Examples of existing bolt or port devices that can be used and/or modified to provide a subdural drainage device to which a housing/stylet may be attached according to embodiments of the present invention include, but are not limited to, the Codman microsensor skull bolt kit (Johnson & Johnson, Raynham, Mass.), the Spiegelberg Probe 3 PS SND (Spiegelberg, Hamburg, Germany), the Integra Ventrix NL950-P parenchymal pressure kit (Integra, Plainsboro, N.J.), and the Integra Bolt Model 110-4B (Integra, Plainsboro, N.J.), and those described in U.S. Pat. No. 6,923,799 to Asfora and U.S. Pat. No. 4,114,603 to Wilkinson. In general, the subdural drainage devices, including catheter supports according to some embodiments of the present invention, may have an opening formed therethrough, and may include an upper portion, a body portion, and a lower portion. The lower portion may be threaded, e.g., with self-tapping threads, for fastening into the skull of a subject. The subdural drainage devices, including catheter supports, may be made of any suitable material including metals, polymers, composites, or combinations thereof. In some embodiments, the housing and subdural drainage device may be combined as a single member.

Subdural Catheters.

Catheter portions of the present invention can take any of a variety of configurations, in accordance with known catheters or variations thereof that will be apparent to those skilled in the art. See, e.g., U.S. Pat. No. 4,573,576 to Krol and U.S. Pat. No. 6,283,940 to Mullholand. Typically the subdural catheter has a proximal end, a distal end (the distal end for positioning in the subdural space), and one or more drain lumens formed therein. The body of the catheter may be elongate and flexible if desired. The stylet (discussed herein) may travel through the catheter in one of the drain lumens, or may travel through the catheter in a separate stylet lumen.

Stylet and Stylet Housing.

Embodiments according to the invention further provide a housing for a stylet (such as in a sealed environment so that the stylet remains sterile during use). The housing may be collapsable. The housing may include an upper portion and lower portion, with the housing lower portion configured to be connected to the catheter support upper portion (e.g., by means of a temporary mechanical connection, friction connection, or combination thereof, which provides a seal suitable for maintaining sterility). In some embodiments the housing has (i) an extended configuration and (ii) a collapsed configuration. A stylet, typically elongate in shape, is positioned inside the sealed housing. The stylet may be formed of any suitable material, and in some embodiments may be flexible. The stylet typically has an upper portion and a lower portion. The stylet and housing together are configured with (i) said stylet in a withdrawn position when said housing is in an extended configuration, and (ii) the stylet in an extended position with the stylet extending completely through said subdural catheter and the stylet lower portion, and engaging and deforming the catheter distal end (at the bumper portion noted above) to disrupt blockages therein when the housing is in its collapsed configuration. Note that the "withdrawn position" of the stylet simply means that the stylet is withdrawn from a portion of the subdural evacuation port device and/or is not deforming the catheter distal end portion: the stylet can still extend partly or completely into the subdural evacuation port device and/or catheter lumen in the withdrawn position.

In some embodiments, the interior diameter of the subdural drainage device (such as a catheter or port) is about 4-5 mm and the diameter of the stylet is significantly smaller, such as about 1-2 mm, so that fluid may flow around the stylet. In some embodiments, the stylet is slightly smaller that the diameter of the subdural drainage device (such as a catheter or port), e.g., to provide a relatively small clearance (such as about 0.5 mm or less) so as to physically remove clotting and/or obstructions in the subdural drainage device. However, any suitably sized subdural drainage device and stylet may be used.

Both the stylet and stylet housing may be rigid or flexible, and formed of any suitable polymeric, metallic, or composite material, or combination thereof. Any suitable diameter stylet may be used. For example, the stylet may be sufficiently small such that fluid flows through the subdural evacuation device and around the stylet even when the stylet is in the extended position. However, in some embodiments, the stylet may have a diameter that is sufficiently large so as to push blockages out of the subdural evacuation port device, for example, as shown in FIGS. 10A-10B with respect to the stylet 520.

While the stylet and stylet housings are generally depicted herein as linear, it will be appreciated that these elements may also take different forms and shapes. Proximal and/or distal end portions of the stylet may be turned, angled, enlarged, and/or shaped to better engate handles, catheter distal end portions, or the like. The body portion of a flexible stylet may be flexed in a radial manner so that the stylet housing need not protrude vertically from the subdural drainage device.

Drains and reservoirs used to carry out the present invention may be any suitable form, including electromechanical devices that apply a negative pressure, simple tube and bulb devices, etc., and may be connected to the subdural drainage system at any suitable position, such as the housing, the subdural drainage device, catheter, catheter support or subdural drainage port. The housing according to embodiments of the present invention may be configured to attach to existing subdural drainage devices, such as a subdural evacuation port system (or "SEPS") available from Medtronic, Inc., Minneapolis, Minn. In some embodiments, drains and/or reservoirs may connect to the external port of the subdural drainage systems described herein in a positive manner that maintains a sterile seal of the device, in like manner as described above.

Although embodiments of the present invention have been described with respect to a subdural evacuation port, it should be understood that the housing and stylet configurations may be used in other devices, including therapeutic agent or drug delivery devices, in which the reservoir may be replaced with a delivery system that flows a fluid out of the device and into a subject in the reverse direction of a drainage system.

Kits of the present invention can include the entire device, assembled or disassembled into components. The device or components thereof may be sealed, together or individually, in sterile packages or containers by any suitable technique. Where components are sealed into two or more separate sterile packages, those separate packages may in turn be packaged together in a larger package that contains multiple components. Printed instructions for use of the system may be included within and/or printed on the packaging, as desired.

REFERENCES

1) Ramachandran R, Thimmappa H. Chronic subdural hematomas—causes of morbidity and mortality. Surg Neurol 2007:67; 367-373.
2) Sucu H K, Gokmen M, Ergin A, Bezircioglu, Gokemn A. Is there a way to avoid surgical complications of twist drill craniostomy for evacuation of a chronic subdural hematoma. Acta Neurochir (Wien) 2007; 149:597-599.
3) Ernestus R I, Beldzinski P, Lanfermann H, Klug N. Chronic subdural hematoma: Surgical treatment and outcome in 104 patients. Surg Neurol 1997; 48:220-225.
4) Mellergard P, Wisten O. Operations and re-operations for chronic subdural haematomas during a 25-year period in a well defined population. Acta Neurochir (Wien) 1996; 138:708-713.
5) Merlicco G, Pierangeli E, di Padova P L. Chronic subdural hematomas in adults: prognostic factors. Analysis of 70 cases. Neurosurg Rev 1995; 18:247-251.
6) Asfora W T, Schwebach L. A modified technique to treat chronic and subacute subdural hematoma: technical report. Surg Neurol 2003; 59:329-332.
7) Lollis S S, Wolak M L, Mamourian A C. Imaging characteristics of the subdural evacuating port system, a new bedside therapy for subacute/chronic subdural hematoma. AJNR Am J Neuroradiol. 2006 January; 27(1):74-5.)

The foregoing is illustrative of the present invention, and is not to be construed as limiting thereof. The invention is defined by the following claims, with equivalents of the claims to be included therein.

That which is claimed is:

1. A subdural drainage system, comprising:
(a) a subdural drainage device having an opening formed therethrough, said subdural drainage device having an upper portion, a body portion, and a lower portion;
(b) a housing having an upper portion and lower portion, with said housing connected to said subdural drainage device; said housing movable between (i) a first configuration and (ii) a second configuration; and
(c) an elongated element positioned inside said housing, said elongated element having an upper portion, a lower portion and a deformable member connected to the lower portion; said elongated element being configured such that said elongated element is moved between (i) a retracted position with said elongated element inside a portion of said subdural drainage device and said deformable member inside said housing, and (ii) an extended position with said elongated element extending through said subdural drainage device such that said deformable member automatically extends to an extended, deformed position in which blockages are disrupted in the subdural drainage device when said housing is moved between said first and second housing configurations; and (d) an external drain opening formed on either said subdural drainage device or said housing.

2. The system of claim 1, wherein said deformable member has a diameter that is greater than a diameter of said housing when said deformable member is in the extended, deformed position.

3. The system of claim 1, wherein said elongated element comprises a stylet.

4. The system of claim 1, wherein said elongated element comprises a catheter.

5. The system of claim 4, wherein:
said elongated element and said housing are connected to one another; and
said elongated element is slidably received in said catheter opening.

6. The system of claim 5, wherein said elongated element, said deformable member and said housing are removably received in said subdural drainage device.

7. The system of claim 1, further comprising a drug delivery device that is removably receivable in said subdural drainage device.

8. The system of claim 1, wherein said housing comprises a rigid telescoping housing.

9. The system of claim 1, wherein said housing comprises a biasing member positioned to bias said enclosed housing in one of said first or second configurations.

10. The system of claim 1, wherein said subdural drainage device lower portion has self-tapping threads formed thereon; and wherein said subdural drainage device comprises an enlarged grasping portion for manually threading said lower portion into the skull of a subject.

11. The system of claim 1, further comprising a reservoir connected to said external drain opening.

12. The system of claim 1, wherein said housing provides a sealed enclosure when said system is connected to a skull of a subject.

13. A occlusion-removal apparatus for use with a subdural drainage device, said apparatus comprising:

(a) an elongated element configured to be inserted in said subdural drainage device; said elongated element having a proximal end and a distal end, with said elongated element having a drain lumen formed therein; and with said distal end having a deformable member having subdural drain openings formed therein, said drain openings in fluid communication with said drain lumen;

(b) a housing connected to said elongated element and having an upper portion and lower portion; and
wherein said elongated element is movable between (i) a retracted position with said elongated element inside a portion of said subdural drainage device and said deformable member inside said housing, and (ii) an extended position with said elongated element extending through said subdural drainage device such that said deformable member automatically extends to an extended, deformed position in which blockages are disrupted in the subdural drainage device when said housing is moved between said first and second housing configurations; and (c) an external drain opening in fluid communication with said housing.

14. The apparatus of claim 13, wherein said housing comprises a rigid telescoping housing.

15. The apparatus of claim 13, wherein said housing comprises a biasing member positioned to maintain said enclosed housing in one of said first and second configurations.

16. A kit comprising an apparatus of claim 1.

17. A kit of claim 16, wherein said apparatus is sealed in one or more a sterile packages or containers.

18. A method for draining the subdural space, said method comprising:
positioning a subdural drainage system on a patient, the subdural drainage system comprising:

(a) a subdural drainage device having an opening formed therethrough, said subdural drainage device having an upper portion, a body portion, and a lower portion;

(b) a housing having an upper portion and lower portion, with said housing connected to said subdural drainage device; said housing movable between (i) a first configuration and (ii) a second configuration; and (c) an elongated element positioned inside said housing, said elongated element having an upper portion and a lower portion and configured such that said elongated element is moved between (i) a withdrawn position with said elongated element withdrawn from a portion of said subdural evacuation port device, and (ii) an extended position with said elongated element extending through said subdural drainage, wherein said elongated element comprises a deformable member on the lower portion thereof; and (d) an external drain opening formed on either said subdural drainage device or said housing; and moving said housing between said first and second housing configurations so that said elongated element is moved between said withdrawn position with said elongated element withdrawn from a portion of said subdural evacuation port device, and said extended position with said elongated element extending through said subdural drainage device, such that said deformable member automatically extends to an extended, deformed position in which blockages are disrupted in the subdural drainage device when said housing is moved between said first and second housing configurations.

* * * * *